(12) United States Patent
Locke et al.

(10) Patent No.: US 10,946,216 B2
(45) Date of Patent: Mar. 16, 2021

(54) INCORPORATING MULTIPLE TARGETS IN TRAJECTORY OPTIMIZATION FOR RADIOTHERAPY TREATMENT PLANNING

(71) Applicants: Varian Medical Systems International AG, Steinhausen (CH); The Board of Trustees of the Leland Stanford Junior University, Office of the General Counsel, Stanford, CA (US)

(72) Inventors: Christopher Barry Locke, Mountain View, CA (US); Santtu Ollila, Helsinki (FI); Karl Kenneth Bush, Palo Alto, CA (US)

(73) Assignees: Varian Medical Systems International AG, Steinhausen (CH); The Board of Trustees of the Leland Stanford Junior University, Office of the General Counsel, Stanford, CA (US)

( * ) Notice: Subject to any disclaimer, the term of this patent is extended or adjusted under 35 U.S.C. 154(b) by 97 days.

(21) Appl. No.: 16/235,205

(22) Filed: Dec. 28, 2018

(65) Prior Publication Data
US 2020/0206531 A1   Jul. 2, 2020

(51) Int. Cl.
*A61N 5/10*   (2006.01)
(52) U.S. Cl.
CPC ......... *A61N 5/1031* (2013.01); *A61N 5/1036* (2013.01); *A61N 5/1047* (2013.01)

(58) Field of Classification Search
CPC .... A61N 5/103; A61N 5/1031; A61N 5/1036; A61N 5/1042; A61N 5/1045; A61N 5/1047
See application file for complete search history.

(56) References Cited

PUBLICATIONS

Locke et al., "Trajectory Optimization in Radiotherapy Using Sectioning (TORUS)", Department of Radiation Oncology, Stanford University School of Medicine, Stanford, CA; Apr. 4, 2017, pp. 1-42; www.delta4family.com.

*Primary Examiner* — Carrie R Dorna
(74) *Attorney, Agent, or Firm* — Kilpatrick Townsend & Stockton LLP

(57) ABSTRACT

Methods of treatment trajectory optimization for radiotherapy treatment of multiple targets include determining beam's eye view (BEV) regions and a BEV region connectivity manifold for each target group of a plurality of target groups separately. The information contained in the BEV regions and the BEV region connectivity manifolds for all target groups is used to guide an optimizer to find optimal treatment trajectories. To improve the visibility of insufficiently exposed voxels of planning target volumes (PTVs), a post-processing step may be performed to enlarge certain BEV regions, which are considered for exposing during treatment trajectory optimization.

20 Claims, 20 Drawing Sheets
(8 of 20 Drawing Sheet(s) Filed in Color)

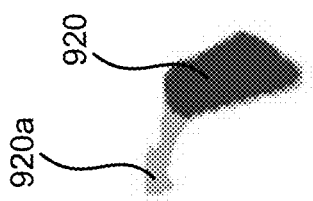
*FIG. 9C*
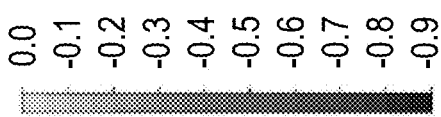
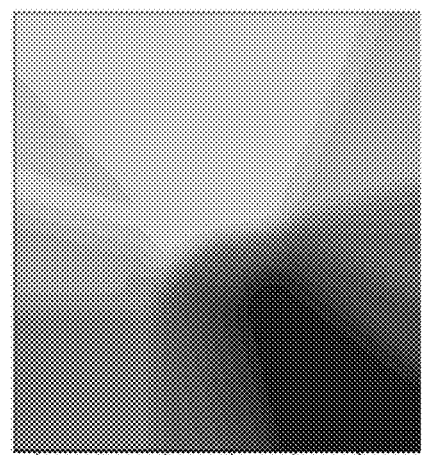
*FIG. 9B*
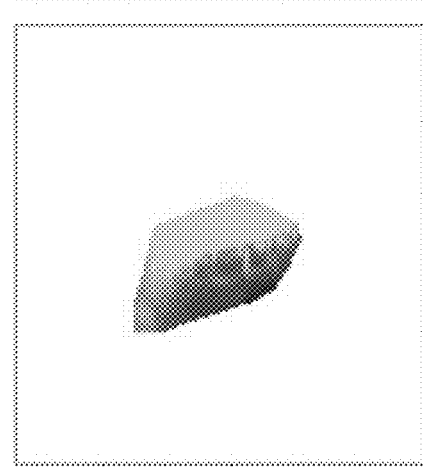
*FIG. 9A*

INCORPORATING MULTIPLE TARGETS IN TRAJECTORY OPTIMIZATION FOR RADIOTHERAPY TREATMENT PLANNING

BACKGROUND

Significant developments have been made in inverse treatment planning of external beam radiation therapies using, e.g., IMRT and VMAT treatment modalities. As both plan quality requirements and requirements on the clinics' patient throughput increase, the role of automation and a higher degree of personalization of treatment plans become increasingly important. Prior to inverse-optimization of the MLC leaf sequence and dose rates in a radiation treatment plan, treatment fields, such as VMAT trajectories or IMRT fields, may need to be selected. The choice of treatment geometry (e.g., isocenter(s), starting and stopping gantry angles, and collimator angle(s) of VMAT arcs, or gantry angle, couch angle, collimator angle, and jaw positions of IMRT fields) may be dictated by a clinical protocol for a given treatment site. Such a protocol may be sub-optimal considering the variability in patient anatomy and in clinical goals. In addition, a radiotherapy treatment may involve multiple tumors or lesions that can have very different volumes. Some of the tumors may be partially or fully spatially overlapping, and some of them may be spatially disjoint. Therefore, there is a need for improved methods of optimizing treatment geometries.

SUMMARY

According to some embodiments, methods for optimizing treatment geometries consider dose response to regions of interest (ROIs). The ROIs may include one or more planning target volumes (PTVs) and one or more organs at risk (OARs). These methods may automate an otherwise formidable amount of manual planning work, and may afford a new realm of dose sculpting that can significantly enhance target dose conformity and reduce toxicity in normal tissue.

In some embodiments, beam's eye view (BEV) regions and a BEV region connectivity manifold are determined by evaluating dose response of each ROI for each vertex in a delivery coordinate space (DCS). The information contained in the BEV regions and the BEV region connectivity manifold is used to guide an optimizer to find optimal field geometries in a radiation treatment plan. According to some embodiments, to improve the visibility of insufficiently exposed voxels of planning target volumes (PTVs), a post-processing step, referred to herein as "coverage boosting," may be performed to enlarge certain BEV regions, which are considered for exposing during treatment geometry optimization.

In some embodiments, to optimize treatment trajectories for radiotherapy treatment of multiple targets, BEV regions and a BEV region connectivity manifold are determined for each target group of a plurality of target groups separately. The BEV regions associated with all target groups make up an entire set of BEV regions, which is then used in the treatment trajectory optimization. By determining BEV regions for each target group separately, a more balanced approach to a complex multi-target treatment may be achieved.

In some embodiments, the information contained in the BEV regions and the BEV region connectivity manifold is used to guide an optimizer to find optimal field geometries in an IMRT treatment plan. The treatment fields may be represented in the optimization framework as a set of nodes. A beam angle optimization (BAO) may involve finding a set of nodes that have an optimal max-distance.

These and other embodiments of the disclosure are described in detail below. For example, other embodiments are directed to systems, devices, and computer readable media associated with methods described herein.

A better understanding of the nature and advantages of embodiments of the present disclosure may be gained with reference to the following detailed description and the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 9A-9C illustrate exemplary steps for calculating locally varying threshold BEV scores according to some embodiments.

DETAILED DESCRIPTION

The present disclosure relates generally to treatment planning for radiation therapy using external-beam radiation treatment systems, and is more particularly directed to optimizing trajectories and field geometries in a radiation treatment plan. Beam's eye view (BEV) regions and a BEV region connectivity manifold may be determined by evaluating dose response of each region of interest for each vertex in a delivery coordinate space (DCS). The information contained in the BEV regions and the BEV region connectivity manifold may be used to generate optimized trajectories or optimized field geometries in a radiation treatment plan.

I. Treatment System

Figure 1:
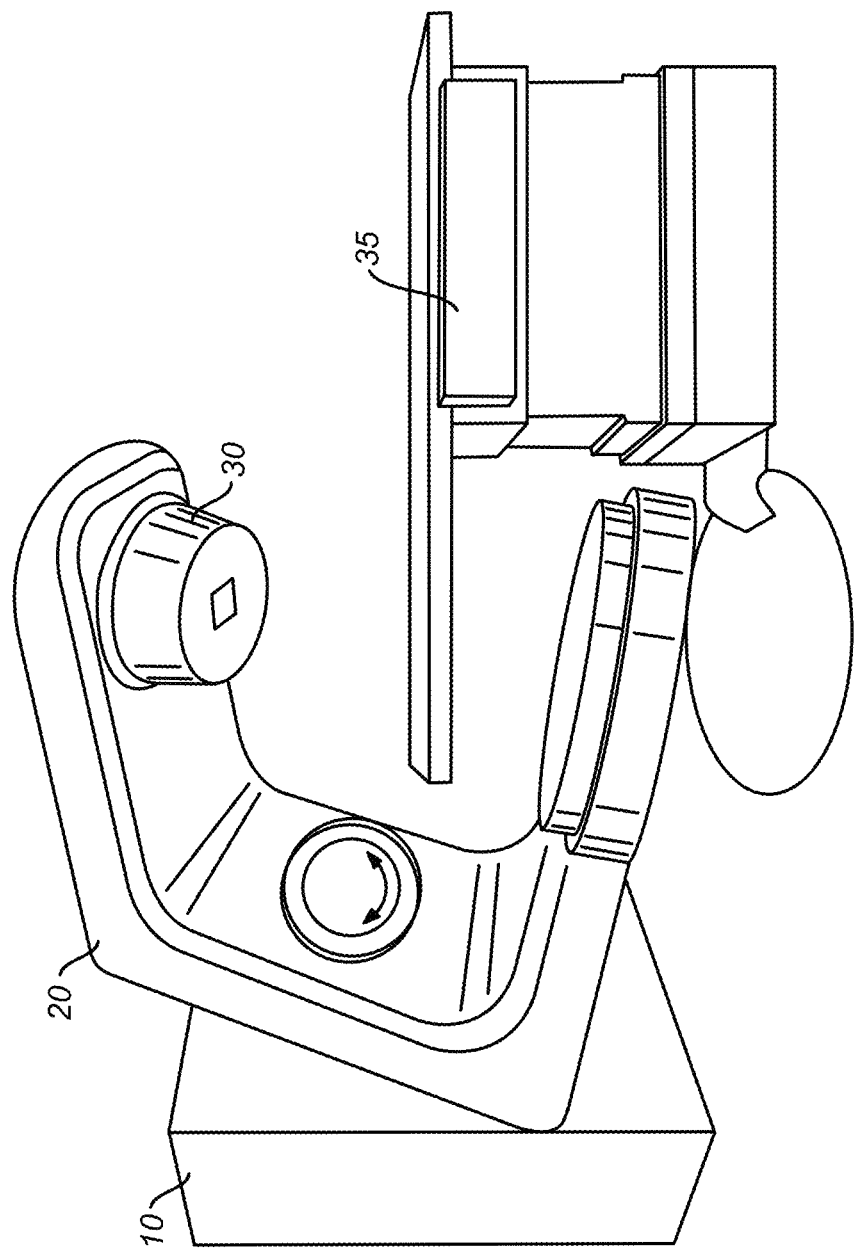
FIG. 1 is a schematic perspective view of a radiation treatment system.
Figure 2:
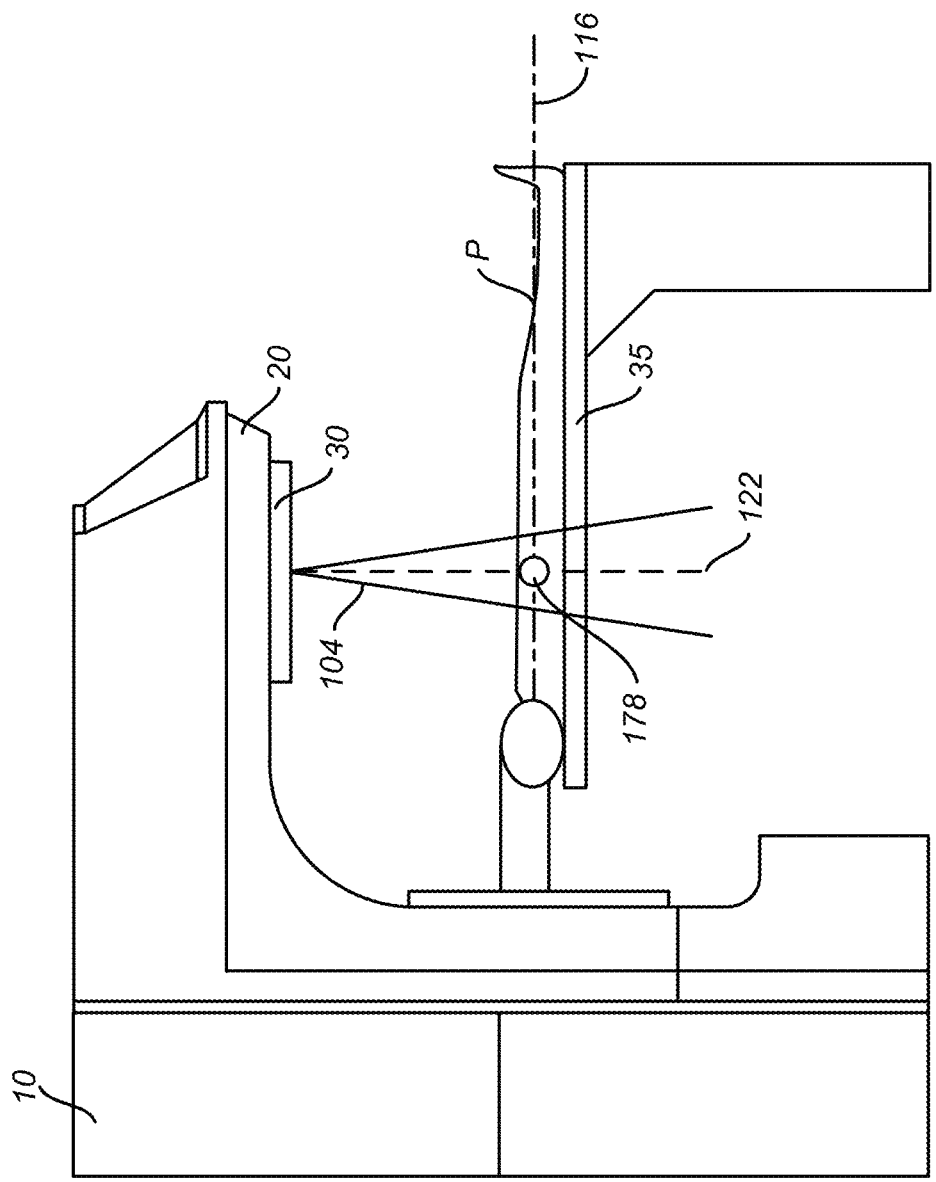
FIG. 2 is a schematic side view of a radiation treatment system.

FIGS. 1 and 2 depict a radiation treatment system of the type that may be used in connection with the present invention. Referring to FIG. 1, a perspective view of radiation treatment system (in this case a linear accelerator) is shown. Typically, such a system is capable of generating either an electron (particle) beam or an x-ray (photon) beam for use in the radiotherapy treatment of patients on a treatment couch 35. Other radiation treatment systems are capable of generating heavy ion particles such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10 there is arranged a control unit (not shown) that includes control circuitry for controlling the different modes of operation of the accelerator. A high voltage source is provided within the stand or in the gantry, to supply voltage to an electron gun (not shown) positioned on an accelerator guide located in the gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Referring now to FIG. 2, a somewhat more detailed side view of a radiation treatment system of the type that may be used in connection with the present invention is shown. A patient P is shown lying on the treatment couch 35. X-rays formed as described above are emitted from the target in the treatment head 30 in a divergent beam 104. Typically, a patient plane 116, which is perpendicular to the page in FIG. 2, is positioned about one meter from the x-ray source or target, and the axis of the gantry 20 is located on the plane 116, such that the distance between the target and the isocenter 178 remains constant when the gantry 20 is rotated. The isocenter 178 is at the intersection between the patient plane 116 and the central axis of beam 122. A treatment volume to be irradiated is located about the isocenter 178.

Figure 3:
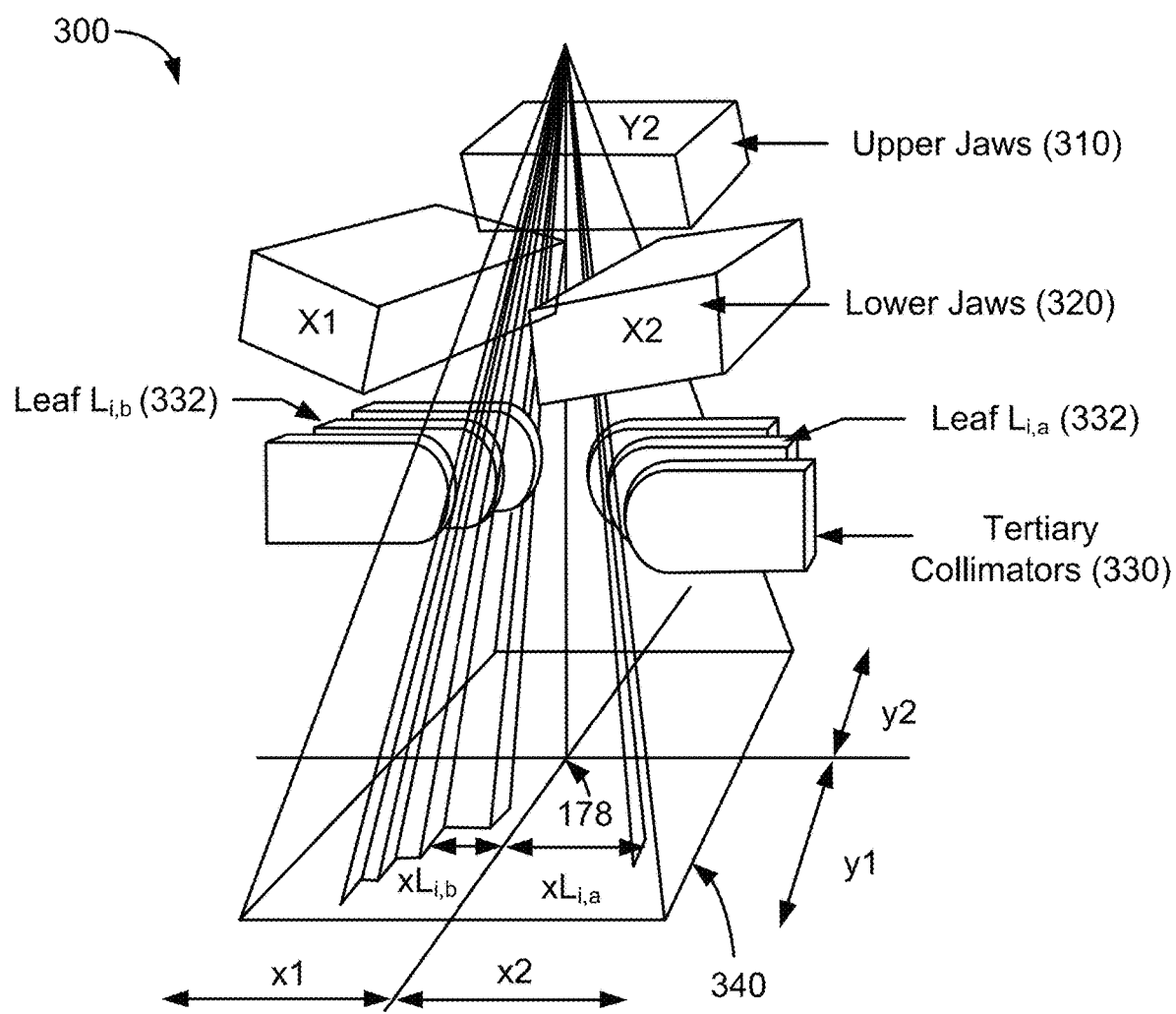
FIG. 3 shows schematically a photon collimation system in a radiation treatment system.

FIG. 3 shows schematically a photon collimation system 300 with upper jaws 310 (i.e., the Y1 and Y2 jaws; the Y1 jaw is omitted for clarity), lower jaws 320 (i.e., the X1 and X2 jaws), and a multi-leaf collimator (MLC) 330. The field dimensions in the plane 340 at the isocenter 178 are indicated. The upper jaws 310, the lower jaws 320, and the leaves 332 of the MLC 330 comprise an x-ray blocking material, and are positioned in the head 30 to define the width of the x-ray beam at the patient plane. Typically, the jaws 310 and 320 are moveable and, when fully open, define a maximum beam of about 40 cm×40 cm at the patient plane 116. The MLC 330 is positioned at the exit of the head 30, to further shape the x-ray beam. Since its introduction in 1990 the MLC has become a standard feature of most radiation treatment systems. An example of a current MLC sold by the assignee of the present invention use up to 120 individually controllable leaves, typically thin slices of tungsten, that can be moved into or out of the x-ray beam under the control of system software.

Figure 4:
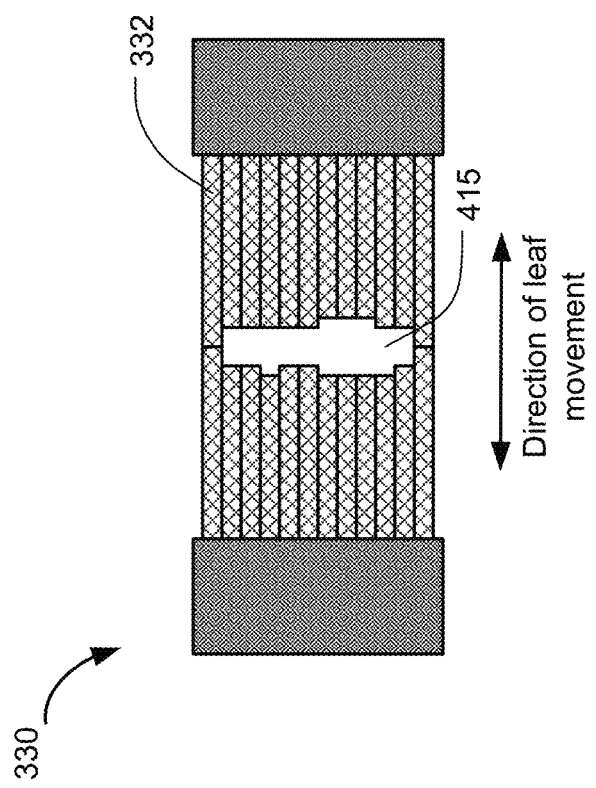
FIG. 4 shows an exemplary multi-leaf collimator (MLC) plane.

FIG. 4 shows an exemplary MLC plane having a plurality of leaves 332, arranged in opposing pairs, and an aperture 415 created by selected leaf movements. Radiation passes through and is shaped by the aperture 415. Thus, the MLC can be used to collimate the x-rays to provide conformal treatment of tumors from various angles ("3D conformal") as well as intensity modulated radiotherapy ("IMRT"), whereby different radiation doses are delivered to different portions of the treatment area. The treatment volume, i.e., the irradiated volume proximate to the isocenter 178 in the path of the x-ray beam, is defined by the jaws 310 and 320, the leaf sequences of the MLC 330, and the collimator angle, i.e., the angle at which the MLC 330 sits in the head 30. Some external radiation treatment systems may include multiple layers of MLCs. The multiple layers of MLCs may be positioned at different planes and at different collimator angles.

Figure 5:
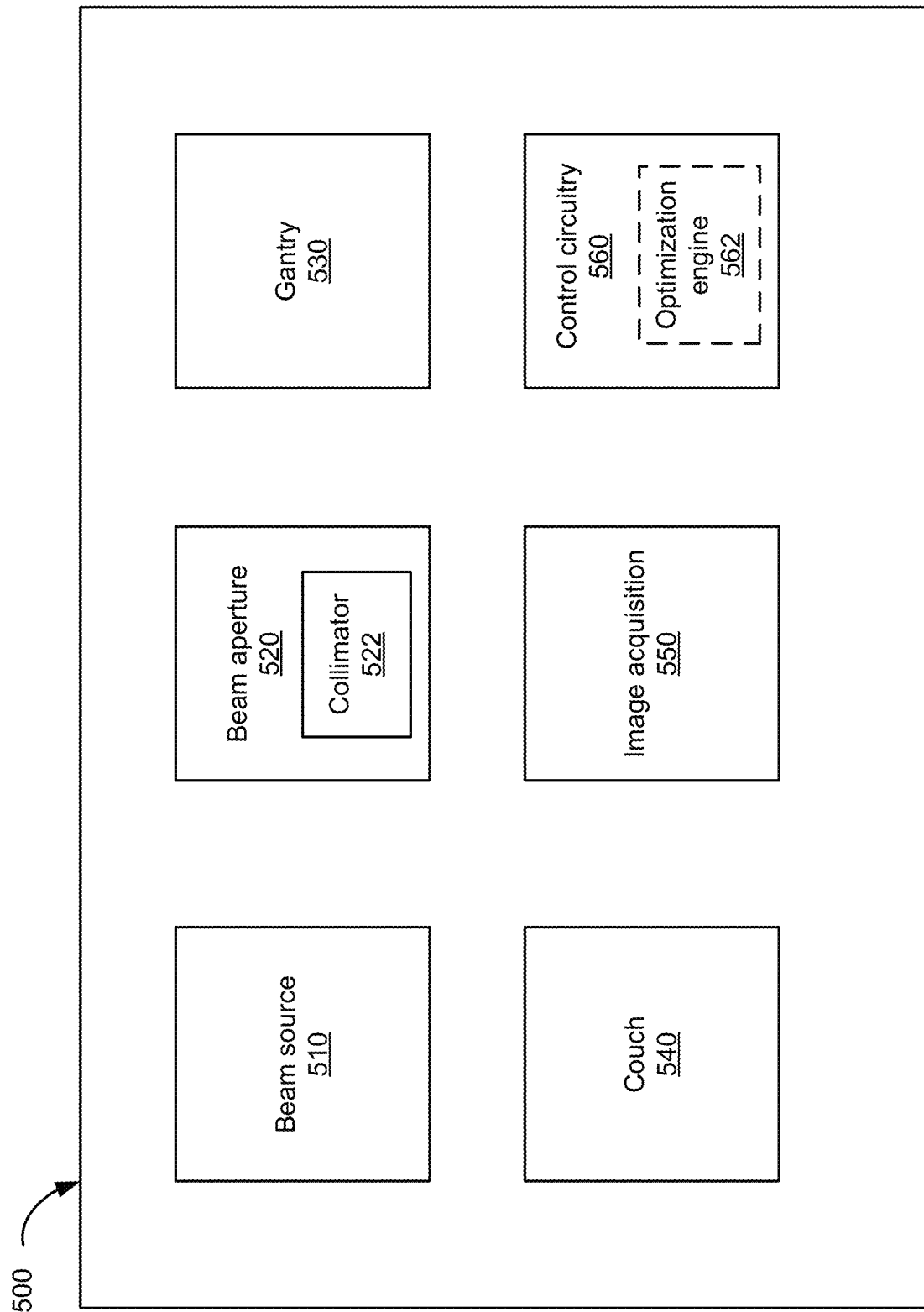
FIG. 5 shows a block diagram of an external-beam radiation treatment system of FIGS. 1 and 2.

FIG. 5 shows a block diagram of an external-beam radiation treatment system 500 of FIGS. 1 and 2. The radiation treatment system 500 includes a beam source 510, a beam aperture 520, a gantry 530, and a couch 540. The beam source 510 is configured to generate a beam of therapeutic radiation. This beam of radiation may include x-rays, particles, and the like. The beam aperture 520 includes an adjustable multi-leave collimator (MLC) 522 for spatially filtering the radiation beam. The couch 540 is configured to support and position a patient. The couch 540 may have six degrees of freedom, namely the translational offsets X, Y, and Z, and the rotation, pitch, and yaw.

The gantry 530 that circles about the couch 540 houses the beam source 510 and the beam aperture 520. The beam source 510 is optionally configured to generate imaging radiation as well as therapeutic radiation. The radiation treatment system 500 may further include an image acquisition system 550 that comprises one or more imaging detectors mounted to the gantry 530.

The radiation treatment system 500 further includes a control circuitry 560 for controlling the operation of the beam source 510, the beam aperture 520, the gantry 530, the couch 540, and the image acquisition system 550. The control circuitry 560 may include hardware, software, and memory for controlling the operation of these various components of the radiation treatment system 500. The control circuitry 560 can comprise a fixed-purpose hard-wired platform or can comprise a partially or wholly-programmable platform. The control circuitry 560 is configured to carry out one or more steps, actions, and other functions described herein. In some embodiments, the control circuitry 560 may include a memory for receiving and storing a radiation treatment plan that defines the control points of one or more treatment fields.

The control circuitry 560 may then send control signals to the various components of the radiation treatment system 500, such as the beam source 510, the beam aperture 520, the gantry 530, and the couch 540, to execute the radiation treatment plan. In some embodiments, the control circuitry 560 may include an optimization engine 562 configured for determining a radiation treatment plan. In some other embodiments, the control circuitry 560 may not include an optimization engine. In those cases, a radiation treatment plan may be determined by an optimization engine in a separate computer system, and the radiation treatment plan is then transmitted to the control circuitry 560 of the radiation treatment system 500 for execution.

II. Radiation Treatment Planning

Radiation therapy is generally implemented in accordance with a radiation treatment plan that typically takes into account the desired dose of radiation that is prescribed to be delivered to the tumor, as well as the maximum dose of radiation that can be delivered to surrounding tissue. Various techniques for developing radiation treatment plans may be used. Preferably, the computer system used to develop the radiation treatment plan provides an output that can be used to control the radiation treatment system, including the control points and the MLC leaf movements. Typically, the desired dose prescribed in a radiation treatment plan is delivered over several sessions, called fractions.

Several techniques have been developed to create radiation treatment plans for IMRT or conformal radiation therapy. Generally, these techniques are directed to solving the "inverse" problem of determining the optimal combination of angles, radiation doses and MLC leaf movements to deliver the desired total radiation dose to the target while minimizing irradiation of healthy tissue. This inverse problem is even more complex for developing arc therapy plans, such as volumetric modulated arc therapy (VMAT), where the one or more external treatment coordinates, such as the isocenter location, gantry angle, couch angles, and couch offsets, are in motion while irradiating the target volume. Heretofore, radiation oncologists or other medical professionals, such as medical physicists and dosimetrists, have used one of the available algorithms to develop and optimize a radiation treatment plan.

Typically, such planning starts with volumetric information about the target tumor and about any nearby tissue structures. For example, such information may comprise a map of the planning target volume ("PTV"), such as a prostate tumor, which is prescribed by the physician to receive a certain therapeutic radiation dose with allowable tolerances. Volumetric information about nearby tissues may include for example, maps of the patient's bladder, spinal cord and rectum, each of which may be deemed an organ at risk (OAR) that can only receive a much lower, maximum prescribed amount of radiation. This volumetric information along with the prescribed dose limits and similar objectives set by the medical professionals are the basis for calculating an optimized dose distribution, also referred to as fluence map, which in turn is the basis for determining a radiation treatment plan. The volumetric information may, for example, be reduced to an objective function or a single figure of merit that accounts for the relative importance of various tradeoffs inherent in a radiation treatment plan, along with constraints that must be met for the radiation treatment plan to be medically acceptable or physically possible.

III. Beam's Eye View (BEV) Sectioning

A. Delivery Coordinate Space (DCS)

State-of-the-art techniques for optimizing treatment trajectories (e.g., VMAT trajectories) in external beam radiation therapy involve dosimetric characterization of candidate directions of incidence. The goal of the optimizations may be to ascertain which directions of incidence in the permissible delivery coordinate space are more suited for treating the patient, considering the dose response of both PTVs and OARs within the patient.

The delivery coordinate space (DCS) is a set of all allowable coordinates that parameterize the delivery device's configuration, truncated to avoid collisions (e.g., machine-to-machine collisions and machine-to-patient collisions). For a C-arm linear accelerator with fixed isocenter, points in a delivery coordinate space may be defined as tuples of the form $(\theta_{gantry}, \theta_{couch})$. The DCS may be discretized into a 2D mesh defined by a set of vertices (gantry, couch values), edges, and triangle faces. Thus, the DCS $\mathbb{D}$ may be represented by a simplicial complex (mesh) defined by:

$N_1^{\mathbb{D}}$ vertices: tuples of $(\theta_{gantry}, \theta_{couch})$ angles;
$N_2^{\mathbb{D}}$ edges: ordered pair of start and end vertices; and
$N_3^{\mathbb{D}}$ triangles: ordered list of 3 vertex indices.

Figure 6:
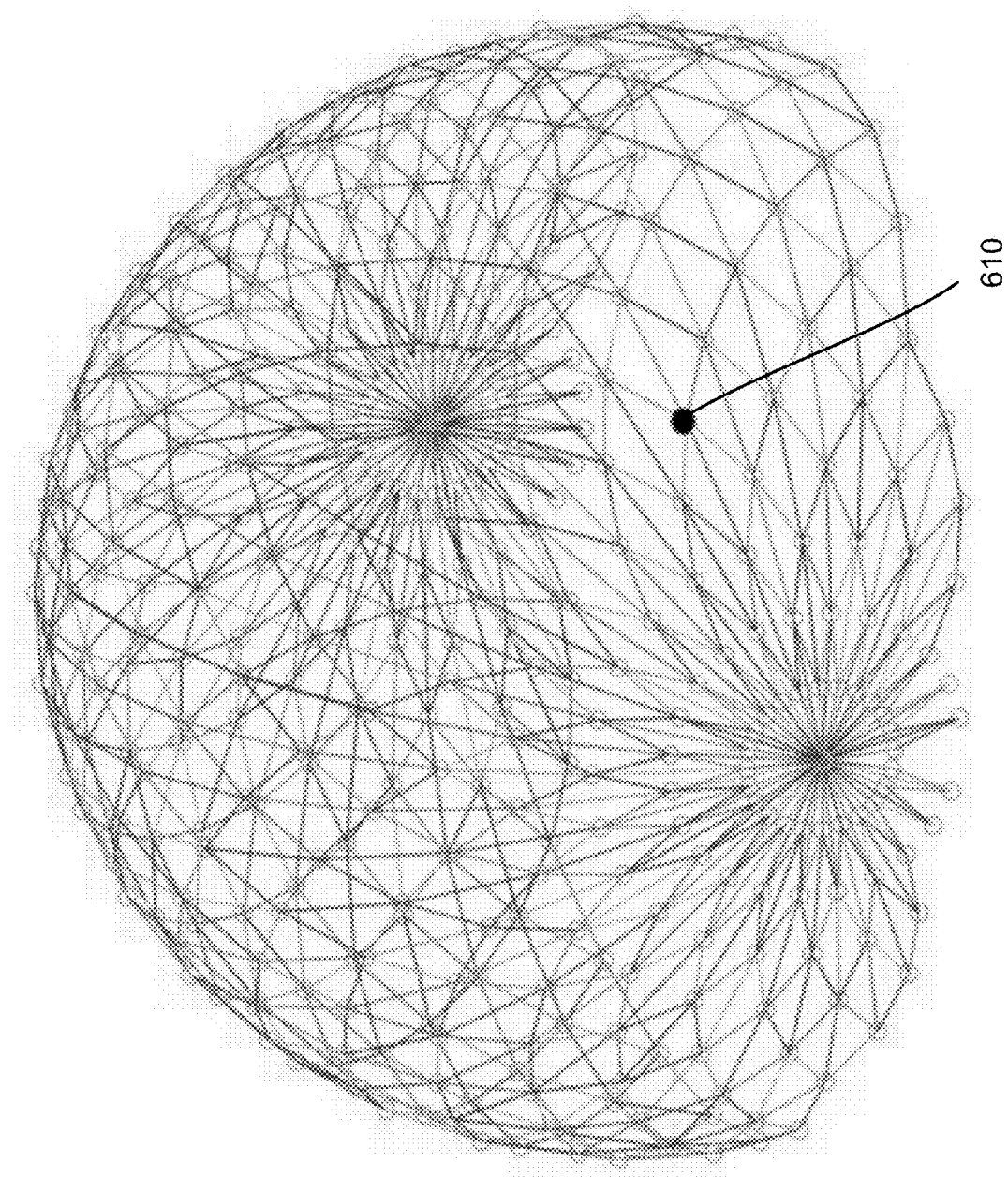
FIG. 6 shows a representation of a delivery coordinate space (DCS) truncated to avoid collisions, where each point ($\theta_{gantry}$, $\theta_{couch}$) is transformed to the physical three-dimensional (3D) location of a treatment head.

FIG. 6 shows a representation of a DCS as a 3D mesh, where each point 610 $(\theta_{gantry}, \theta_{couch})$ is transformed to the physical three-dimensional (3D) location of the treatment head, and the space is truncated to avoid collisions.

B. BEV Sectioning

Reference [1] discusses a method of trajectory optimization in radiotherapy using sectioning (referred herein as TORUS). Dosimetry experience in radiation treatment planning has shown that BEV offers a valuable tool in determining the geometrical setup for both dynamic gantry treatment (e.g., VMAT) and static gantry treatment (e.g., IMRT).

For a source position $r_v^s$ corresponding to vertex v in the 3D DCS, a BEV plane (also referred to as an isocenter plane) may be defined as a plane perpendicular to the vector $r_v^s - r_v^{ISO}$ and including the isocenter $r_v^{ISO}$. A BEV plane may be discretized into a 2D array of $N_x \times N_y$ pixels, with each pixel on this 2D grid representing a single beamlet.

To probe all possible beamlets, the intensity of each beamlet may be set to unity, and a 3D dose response to each beamlet may be evaluated. The 3D dose may be processed to determine dose statistics to each region of interest (ROI) for each beamlet. The ROIs may include, for example, planning target volumes (PTVs) and organs at risk (OARs). If the dose for a beamlet at $(n_x, n_y)$ in the BEV plane given by delivery coordinate vertex $n_v$ to the ROI with index $n_{ROI}$ at position (x,y,z) is given by $D_{n_v, n_x, n_y, n_{ROI}}(x,y,z)$, then the volume integrated dose for the ROI with index $n_{ROI}$ may be evaluated as, $$\mathcal{D}_{n_v, n_x, n_y, n_{ROI}} = \int dx dy dz D_{n_v, n_x, n_y, n_{ROI}}(x,y,z). \quad (1)$$

If there are $N_{ROI}$ regions of interest, then the BEV dose bundle section $\mathcal{D}$ is a 4D array of size $(N_1^{\mathbb{D}}, N_x, N_y, N_{ROI})$ containing the volume integrated dose values for each ROI from each beamlet.

In some embodiments, a BEV score bundle section $S$ may be defined as a contraction of the 4D BEV dose bundle section $\mathcal{D}$ into a 3D matrix of size ($N_1^{\mathcal{D}}$, $N_x$, $N_y$), where the values are a measure of the "goodness" of beamlets based on the ROI dosimetrics. In some embodiments, the "goodness" score may be evaluated as a linear combination of the doses to each ROI, $$S_{n_v,n_x,n_y} = \sum_{n_{ROI}=1}^{N_{ROI}} w_{n_{ROI}} \mathcal{D}_{n_v,n_x,n_y,n_{ROI}}. \quad (2)$$

The coefficients $w_{n_{ROI}}$ may be set by users. For example, the values of the coefficients may be set to −0.2 for body, between −1 and −10 for an OAR (e.g., critical organs may be given more negative weights), and between zero and +1 for a PTV.

C. BEV Region Connectivity Manifold

A BEV region connectivity manifold may be constructed in two steps. First, information contained in the BEV score bundle sections may be considered and a binary selection procedure is applied to determine if a given pixel (beamlet) is a "good" or "bad" candidate for treatment. For each BEV plane, a set of "good" beamlets form regions. Each region includes a set of contiguous pixels in the BEV plane, and represent potential open aperture candidates for use in the optimization. Next, how the regions connect to other regions in neighboring vertices may be determined. The resulting structure, comprised of regions and their connections, forms a BEV region connectivity manifold.

1. BEV Region Score

In some embodiments, a beamlet may be deemed a "good" candidate if it intersects a PTV and its score $S$ is above a certain threshold $S_{threshold}$. Choosing an appropriate threshold may be a non-trivial task and can be case specific. For example, beamlets treating a superficial target with very little body or OAR in the way (e.g. a prone breast irradiation) may have a different threshold than a deep seated target (e.g., in a prostate treatment) in which the best possible plan may still treat through healthy tissue to a substantial depth.

According to some embodiments, a region score $\mathcal{R}_{n_v,n_x,n_y} \in (-\infty, 1]$ may be used to define regions, where the potentially "good" beamlets are defined to have $\mathcal{R} > 0$, $$\mathcal{R}_{n_v,n_x,n_y} = \quad (3)$$

$$\begin{cases} -\infty & \text{if } \nexists\, n_{ROI} \in N_{PTV} \ni \mathcal{D}_{n_v,n_x,n_y,n_{ROI}} > 0 \\ \dfrac{S_{n_v,n_x,n_y} - S_{threshold}}{\max(S) - S_{threshold}} & \text{otherwise} \end{cases},$$

where $N_{PTV}$ is the set of ROI indices for PTV regions of interest. Thus, a beamlet may be deemed a "good" candidate if it intersects the PTV and its score is above some threshold $S_{threshold}$. The region score $\mathcal{R}$ may classify beamlets into regions, and may also act as a normalized score for the goodness of beamlets (e.g., the maximum region score being unity).

2. Score Threshold Determination

According to some embodiments, the score threshold $S_{threshold}$ may be automatically determined using histograms of the BEV fiber bundle sections, in the spirit of dose-volume histograms (DVHs). Given a section $\mathcal{F}_n$, where $n$ is an index in some set $\mathcal{N}$, and a subset of indices under consideration $\mathcal{N}_h$, the associated BEV fiber bundle section histogram may be defined as follows:

Determine the maximum and minimum values of the set $\{\mathcal{F}_n \mid n \in \mathcal{N}_h\}$, $F_{max}$ and $F_{min}$.

Create $N_{bins}$ that range from $F_{min}$ to $F_{max}$, and initialize each to 0. These may be referred to as differential histogram bins and are denoted $\partial B_{n_{bins}}^{\mathcal{F}}$ for each bin index $n_{bin}$.

Loop through each $n \in \mathcal{N}_h$ and increment the bin that corresponds to the value $\mathcal{F}_n$ by 1.

The integrated histogram bins may be defined as $$B_{n_{bin}}^{\mathcal{F}} = \sum_{n=n_{bin}}^{N_{bins}-1} \partial B_n^{\mathcal{F}}.$$

Normalize the differential and integrated histogram bins to have maximum value of 1.

Figure 7:
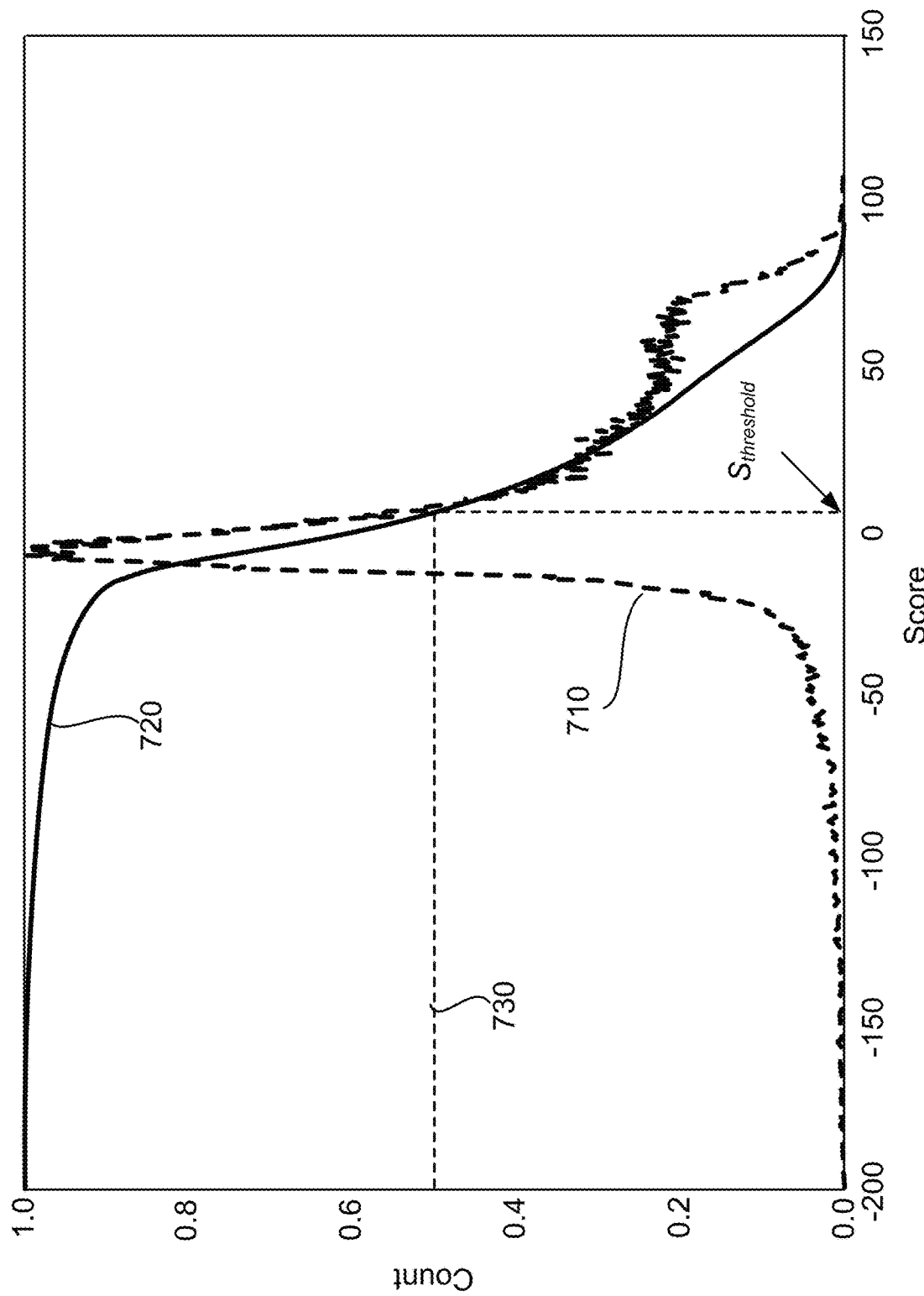
FIG. 7 shows examples of a differential beam's eye view (BEV) fiber bundle section histogram and an integrated BEV fiber bundle section histogram according to some embodiments.

FIG. 7 shows examples of a differential BEV fiber bundle section histogram 710 (dashed line) and an integrated BEV fiber bundle section histogram 720 (solid line) according to some embodiments. The dotted lines 730 meet at the integrated histogram curve 720 and may have a vertical height to horizontal length ratio of 0.7. Their intersection with the abscissa may give the score threshold $S_{threshold}$.

Using this definition, one may define the BEV PTV dose histogram from the BEV fiber bundle section $\mathcal{D}_{n_v,n_x,n_y} = \sum_{n_{ROI} \in N_{PTV}} \mathcal{D}_{n_v,n_x,n_y,n_{Rol}}$ (the BEV fiber bundle section representing the total PTV dose only). These histograms may be denoted as $\partial B^{\mathcal{D}}$ and $B^{\mathcal{D}}$. In some embodiments, this histogram may be used to determine a temporary PTV dose threshold so that only the scores of beamlets with the highest 50% of PTV doses are considered. This threshold value may be denoted $D_{threshold}^{PTV}$ and is the dose of the integrated histogram bin of $B^{\mathcal{D}}$ with height 0.5.

Next, a thresholded BEV score histogram may be calculated using the BEV score bundle section $S$, restricted to the indices $\{n \mid \mathcal{D}_{n_v,n_x,n_y} > D_{threshold}^{PTV}\}$. These thresholded histograms may be denoted as $\partial B^S$ and $B^S$. The ratio of vertical height to horizontal height of a point on the integrated histogram curve (e.g., the ratio of sides of the rectangle formed by the axes and the dotted lines 730 shown in FIG. 7) is:

$$\text{ratio}(S) = B^S(S) \cdot \frac{S_{max} - S_{min}}{S - S_{min}}, \quad (4)$$

where $B^S(S)$ denotes the integrated histogram height at score value $S$ (i.e. where $n_{bin}$ is the corresponding bin index). This ratio varies monotonically from $+\infty$ for $S=S_{min}$ to 0 for $S=S_{max}$ where $B^S=0$. The score threshold $S_{threshold}$ may be defined to be the value such that ratio($S_{threshold}$)=0.7.

It should be understood that the score threshold determination method described above is only an example. Other determination methods may be used according to other embodiments.

Figure 8B:
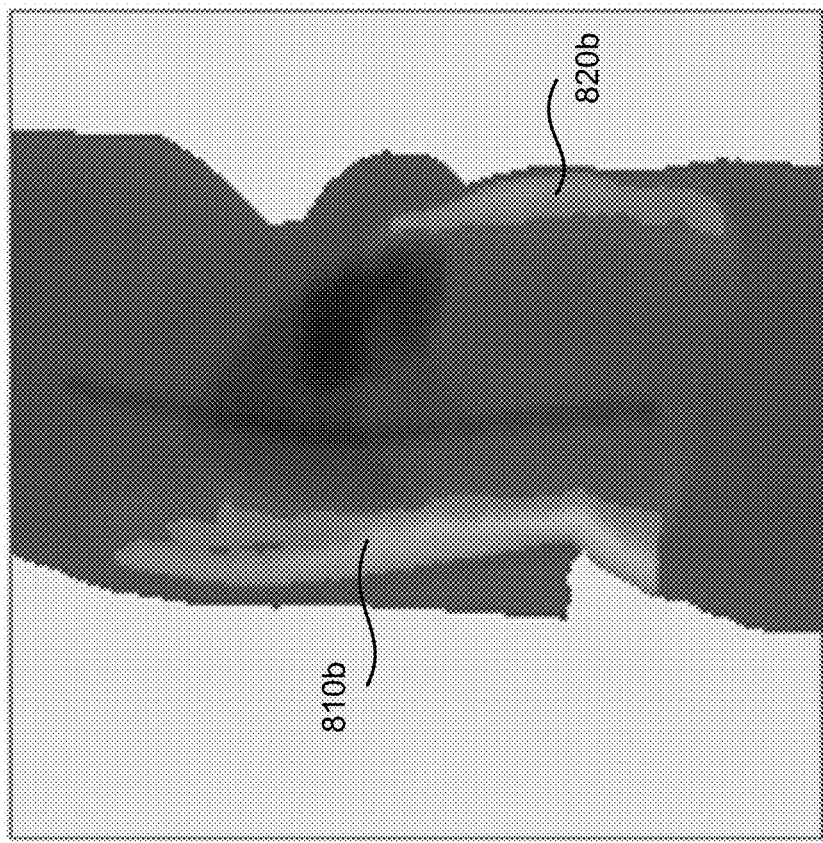
FIGS. 8A and 8B show exemplary images of BEV scores for two adjacent delivery coordinate vertices for a chest wall treatment, respectfully, according to some embodiments.
Figure 8A:
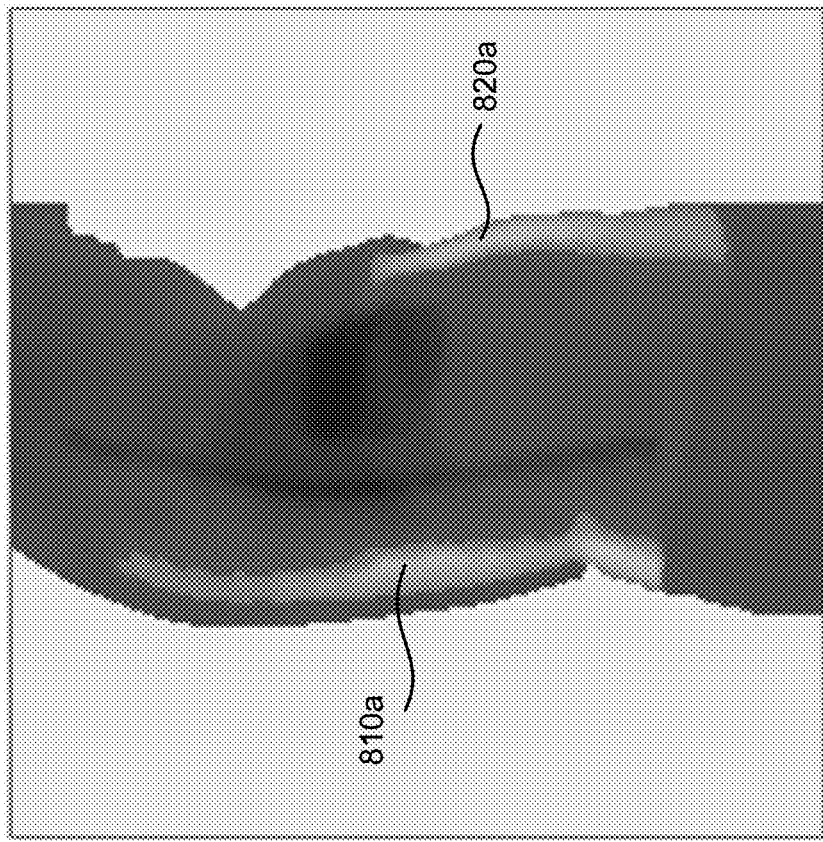

FIGS. 8A and 8B show exemplary images of BEV scores for two adjacent delivery coordinate vertices for a chest wall treatment. Darker shades represent lower score values and brighter shades represent higher score values. Gold colors represent beamlets that pass the region selection criterion, and thus are considered as BEV regions. In this example, from the BEV perspective, there are two disconnected BEV regions 810a and 820a in the BEV shown in FIG. 8A, and two disconnected BEV regions 810b and 820b in the BEV shown in FIG. 8B.

3. BEV Region Connectivity Manifold

Regions at neighboring vertices in the delivery coordinate space may be stitched together to form a complete BEV region connectivity manifold. The BEV region connectivity manifold contains information on how candidate target regions in the BEV change, appear, split, and vanish as one moves along the delivery coordinate space in all directions. For instance, in the example shown in FIGS. 8A and 8B, overlaying the two images of the two adjacent delivery coordinate vertices on each other, the regions 810a and 810b on the left may overlap with each other, and the regions 820a and 820b on the right may overlap with each other. Thus, it may be inferred that the regions 810a and 810b are connected, and the regions 820a and 820b are connected when moving along this edge in delivery coordinate space. The set of all regions and all connections along delivery coordinate space edges form the BEV region connectivity manifold.

The information contained in the BEV regions and the BEV region connectivity manifold may be used to generate optimized trajectories or field geometries in a radiation treatment. For example, as discussed below and in Reference [1], methods of trajectory optimization may use a BEV region connectivity manifold as a scaffold to guide an optimizer, which may make the search space small enough to apply graph search techniques with efficient computation times.

D. Coverage Boosting

As discussed above, beamlets that intersect a PTV and have a BEV score above a global threshold BEV score may be considered desirable and included in BEV regions, which may be considered for exposing during treatment trajectory optimization. This procedure may not guarantee that each elemental volume (e.g., voxel) of a PTV can be irradiated from sufficiently many directions of incidence.

According to some embodiments, to improve the visibility of insufficiently exposed PTV voxels of PTVs, a post-processing step, referred to herein as "coverage boosting," may be performed to enlarge certain BEV regions. Coverage boosting may be achieved by establishing a coupling between the voxels of each PTV group and the BEV regions, as described below.

To preferentially boost PTV coverage of the BEV regions, beamlet-to-beamlet variations in the threshold BEV score may be introduced by considering 3D directions of incidence on each PTV. According to some embodiments, locally varying threshold BEV scores may be calculated as follows. Letting the total number of beams under consideration be $N_b$, a coverage fraction p may be defined (e.g., 0.3) such that the minimum number of beams which may expose each PTV voxel is $pN_b$. Each PTV voxel may be projected onto the BEV score map for each beam under consideration and its distribution of scores may be calculated. Since the goal is to expose $pN_b$ beams, a voxel-specific threshold BEV score which exposes $pN_b$ beams may be determined using the voxel's BEV score distribution, denoted as St for the $i^{th}$ voxel. Assuming $S_{threshold}$ is the original global threshold, then the true voxel-specific threshold is defined to be $S_i$=min $(S'_i, S_{threshold})$.

These voxel-based score thresholds $S_i$ may be used next to define locally varying threshold BEV scores. First, the voxels are projected as points onto each BEV, then pixels inside their tessellation are defined using linear interpolation and pixels outside using nearest-neighbor interpolation. To smooth out artifacts introduced by pixel grid disagreements, a small amount of Gaussian smoothing may be applied to obtain the final locally varying score threshold maps. Regions may then be defined to be the sets of pixels that intersect the PTV and have score above its local threshold value.

FIGS. 9A-9C illustrate the exemplary steps in the calculation of locally varying score thresholds as described above. The image in FIG. 9A shows the result of applying PTV voxel point tessellation internal linear interpolation (0.0 corresponds to original global threshold value); the image in FIG. 9B shows the result of including external nearest neighbor interpolation along with Gaussian smoothing; and FIG. 9C illustrates the resulting increase in region shape when the new locally varying score threshold is used. The area 920 in blue shown in FIG. 9C indicates the BEV region before coverage boosting, and the area 920a in pink shown in FIG. 9C indicates the enlarged BEV region after coverage boosting.

Figure 10B:
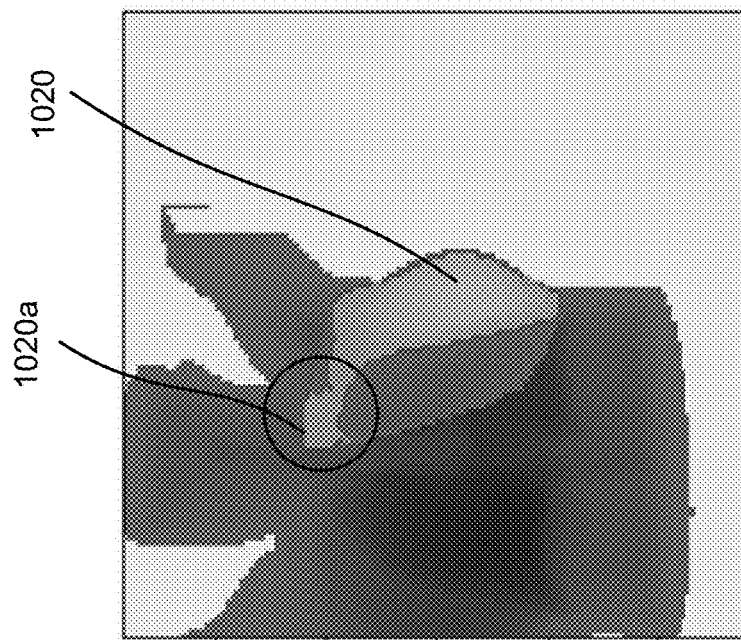
FIGS. 10A-10B illustrate examples of a region (represented by the area in gold color) in a breast and supraclavicular node treatment before coverage boosting is applied (FIG. 10A), and a region after coverage boosting is appled (FIG. 10B), according to some embodiments.
Figure 10A:
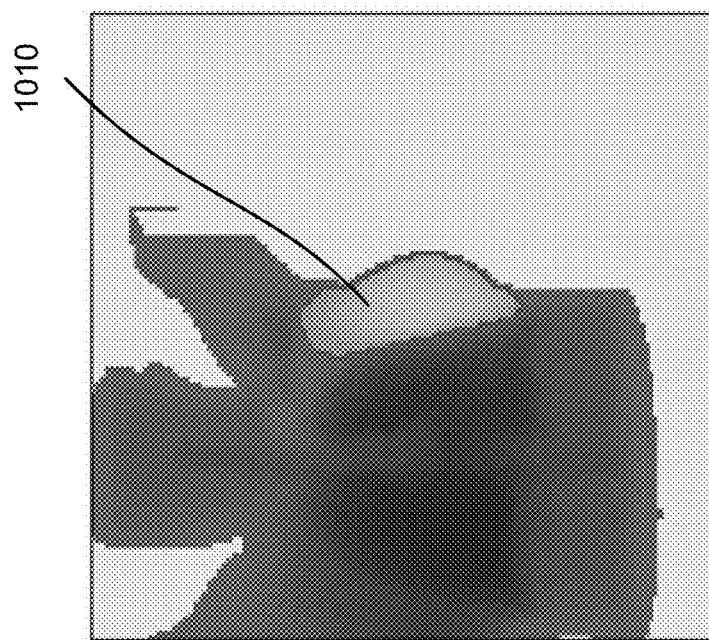

FIGS. 10A-10B illustrate examples of a BEV region 1010 (represented by the area in gold color) in a breast and supraclavicular node treatment before coverage boosting is applied (FIG. 10A), and a region 1020 after coverage boosting is appled (FIG. 10B). As illustrated, the BEV region 1020 after coverage boosting is enlarged as compared to the BEV region 1010 before coverage boosting. For example, the sub area 1020a (corresponding to the smaller supraclavicular nodes in this case) shown in FIG. 10B is not included in the BEV region 1210, and thus those voxels may be "under-hit" by beamlets. After coverage boosting, those voxels may be sufficiently exposed to radiation.

IV. Trajectory Optimization for Radiotherapy Treatment

Reference [1] discusses trajectory optimization in radiotherapy using sectioning (referred herein as TORUS). The TORUS methods use the the BEV regions and BEV region connectivity manifold as a guide to generate heuristically optimal radiotherapy trajectories automatically for efficient delivery of high quality VMAT treatment plans. TORUS uses an optimization graph on top of a delivery coordinate space to generate optimal treatment trajectories using a dual-metric optimization. Nodes in the optimization graph may represent individual control points, and trajectories may be defined as paths that minimize a min-distance metric, while a max-distance metric may act as a measure of goodness to select optimal trajectories.

A. PTV Angular Flux

One of the concepts used in the TORUS methods is PTV angular flux, which relates to novelty of three-dimensional (3D) direction vectors of incident beamlets for a given point in a PTV. Inverse dose optimization may perform better with more angles from which radiation beams enter the patient. The reason for this may be twofold. First, by entering the patient from many directions, the ratio of overlapping dose within the PTV to surrounding OAR may be greater, resulting in steeper dose gradients outside the PTV. Second, each beamlet from each direction may provide a different 3D dose contribution to the patient. Therefore, increasing the number of such unique beamlets may give the optimizer more "basis vectors" to work with when sculpting optimal dose profiles around critical structures.

Note that just entering the patient from many directions may not be sufficient to ensure optimal plan quality. It may be that in some cases, portions of the PTV are only able to be exposed from a small number of directions when protecting nearby OAR, even though the number of beams entering the patient is high. This can result in either under coverage of small regions of the PTV, non-conformal regions (dose streaks), or unsatisfactory dose compensation.

To encourage maximal coverage and conformality, it may be desirable to have each elemental volume of the PTV be individually targeted from many different directions.

Figure 11:
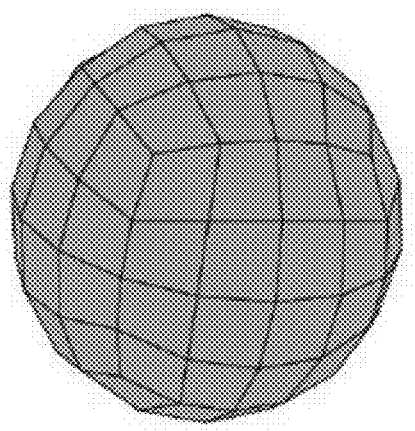
FIG. 11 illustrates an exemplary quadrilateralized spherical cube that may be used for evaluating the angular flux according to some embodiments.

According to some embodiments, an angular flux of a given point in a PTV may be evaluated by computing the 3D direction vectors of incident beamlets and binning them in angular bins. FIG. 11 illustrates an exemplary quadrilateralized spherical cube that may be used for evaluating the angular flux. As illustrated, each cube face may be divided into 4×4 squares. Thus, there are 6×4×4=96 squares. Each square corresponds to a single angular bin. This may provide a bin size on the order of 20 degrees, which may correspond to the same order of distance between vertices in a delivery coordinate space (DCS). In a general case, each cube face may be divided into $2^{2n}$ squares, where n is a positive integer. In the example illustrated in FIG. 11, n=2. This binning method may result in bins of unequal solid angles, but the differences may be relatively small (at most 19%). Additionally, randomly orienting each spherical cube across a set of sampling points may cancel out such discrepancies. In other embodiments, the angular flux may be evaluated by computing the 3D direction vectors of incident beamlets through a closed surface of a shape other than the quadrilateralized spherical cube. For example, the closed surface can be a spherical surface or a cube surface.

A set of sampling points may be distributed within a PTV. The angular flux at each sampling point may be evaluated and optimized during trajectory optimization. According to some embodiments, indexing each bin from 0 to 95, the angular flux of a given PTV point may be stored as a 12 byte bitset, enabling fast bitwise calculations to be performed. If there are n PTV points considered, then the angular flux state $\mathcal{A}$ is represented as a vector of length n of bitsets each with 96 bits.

B. Dual-Distance Metric

According to some embodiments, the information stored in the BEV score bundle sections and the BEV region connectivity manifold may be used to generate treatment plans for radiotherapy. The BEV region connectivity manifold may serve as a scaffold to guide the optimizer, which may make a search space small enough to apply graph search techniques with fast computation times.

In general, optimal trajectories in a VMAT-like treatment may be ones that hit the PTV as much as possible, avoid or minimize healthy tissue doses, and enter the PTV from many different directions, and can be completed in a relatively short delivery time. Some of the goals may conflict with each other. For example, a treatment plan that treats each PVT element from every direction with a high degree of MLC modulation may produce a nearly ideal dose distribution, but may also take an excessive amount of time to deliver. Therefore, it may be desirable to find a trajectory that covers many directions around the patient in an efficient way. According to some embodiments, an optimization method may seek to maximize trajectory length, while using relatively "straight" trajectories for delivery efficiently. The "straightness" of a trajectory may be understood in terms of a geodesic line. A geodesic is the shortest path between two given points in a curved space. A geodesic may be calculated by finding a line that minimizes a distance function between the two points.

According to some embodiments, based on the BEV score bundle sections and the BEV region connectivity manifold, trajectories that have control points traversing through regions of high region scores $\mathcal{R}$ may be preferred (e.g., as defined in Equation (3)). To encourage geodesics to traverse such control points, a distance function may be defined such that smaller non-negative distances are preferred. On the other hand, to pick long trajectories, another distance function may be defined such that larger distances are preferred.

To overcome this inherent conflict between trying to find "short" as well as "long" trajectories, a dual-distance metric approach is used in an optimization according to some embodiments. The dual-distance metric includes two distance functions that play different roles in the optimization. The two distance functions may be referred to as a min-distance function $D^{min}$ (where smaller values are preferred; minimization defines geodesic paths in a graph), and a max-distance function $D^{max}$ (where larger values are preferred; to be maximized through selection of trajectory).

C. Stateful Graph Optimization

According to some embodiments, a symmetric directed graph may be used for trajectory optimization using the min-distance function $D^{min}$ and the max-distance function $D^{max}$. Since the distance functions may depend not just on the edges of the graph, but also on the history of a trajectory up to that point, a statefulness may be introduced to the graph.

The graph may include a set of nodes, and a set of edges that connect the nodes. To account for the history in the graph, a point may be defined to be a node and state pair $P=(N, \mathcal{A})$. The state may be the PTV angular flux state described above. Given a point $P_1=(N_1, \mathcal{A}_1)$ and an edge $E=(N_1, N_2)$, the successor point is $P_2=(N_2, \mathcal{A}_2)$, where the new state $\mathcal{A}_2$ may be given by a successor state function $\sigma(\mathcal{A}_1, E)$, which describes how the state changes moving along the edge E. The min-distance and max-distance between these two points may be denoted as $D^{min/max}(P_1, P_2)$ A path may be an ordered sequence of points, P $(P_1, \ldots, P_n)$ such that $\exists E=(N_i, N_{i+1})$ and $\mathcal{A}_{i+1}=\sigma(\mathcal{A}_i, (N_i, N_{i+1}))$ for all $1 \leq i < n$. The min-distance and max-distance of this path may be $D^{min/max}(P)=\Sigma_{i=1}^{n-1} D^{min/max}(P_i, P_{i+1})$. Given an initial state $\mathcal{A}$ and two nodes N and N', let the set of all possible paths between them, $P(P_1, \ldots, P_n)$ such that $P_1=(N, \mathcal{A})$ and $P_n=(N', \mathcal{A}')$, where $\mathcal{A}'$ is unspecified, be denoted $\mathcal{P}(N, N' | \mathcal{A})$. A set of trajectories may be defined to be the set of paths with a minimal min-distance, $$\mathcal{T}_{(N,N' | \mathcal{A})} = \arg\min_{P \in \mathcal{P}(N,N' | \mathcal{A})} D^{min}(P). \quad (5)$$

A set of optimal trajectories between these two nodes may then be defined to be the trajectories with a maximum max-distance, $\max_{P \in \mathcal{T}(N,N' | \mathcal{A})}$ $$\mathcal{T}^{optimal}(N,N' | \mathcal{A}) = \arg\max_{P \in \mathcal{T}(N,N' | \mathcal{A})} D^{max}(P). \quad (6)$$

Using the definitions provided by Equations (5) and (6), the min-distance and max-distance between two arbitrary nodes is $D^{min/max}(N,N' | \mathcal{A}) = D^{min/max}(P)$ for $P \in \mathcal{T}^{optimal}(N,N' | \mathcal{A})$.

Given an initial state $\mathcal{A}$, the goal now may be to define a globally optimal trajectory. If attention is restricted to start and end nodes in some set $\mathcal{B}$, then a set of optimal trajectories ending on the set $\mathcal{B}$ may be defined to be:

$$\mathcal{T}_{\mathcal{B}}^{optimal}(\mathcal{A}) \cup_{(N,N') \in \varepsilon_{\mathcal{B}}^{optimal}} \mathcal{T}^{optimal}(N,N' | \mathcal{A}) \quad (7)$$

where $\varepsilon_{\mathcal{B}}^{optimal} = \arg\max_{(N,N') \text{ for } N,N' \in \mathcal{B}} D^{max}(N,N' | \mathcal{A})$.

The optimization problem may be to find an element of $\mathcal{T}_{\mathcal{B}}^{optimal}(\mathcal{A})$ for some initial state $\mathcal{A}$ and the set of start and end points $\mathcal{B}$.

D. Graph Definitions

According to some embodiments, a control point in the graph may be uniquely determined by three integers, vertex v (i.e., a point on the delivery coordinate space or DCS), collimator index c (which determines collimator angle out of a discrete set of possibilities), and region bitfield b. The region bitfield b is a list of boolean flags that determine which subset of regions to select for a given vertex. These three integers may define a node in the graph as $N=(v,c,b)$. Starting MLC leaf positions may be determined by fitting to this subset of regions of the BEV.

According to some embodiments, the BEV region connectivity manifold may include multiple mutually disjoint connected components, each of which forms a single connected part of the total search graph through the following definition of edges. Given two nodes $N_1=(v_1,c_1,b_1)$ and $N_2=(v_2,c_2,b_2)$, there may be an edge E connecting these two nodes if the following are satisfied:

There is an edge connecting $v_1$ and $v_2$ in the delivery coordinate space;

$\Delta t_{collimator} \leq \Delta t_{directional}$, where $\Delta t_{collimator}$ is the time for the collimator to move $\Delta \theta_{collimator} = \theta_{collimator}(c_2) - \theta_{collimator}(c_1)$, and $\Delta t_{directional}$ is the time to move in gantry and couch space from vertex $v_1$ to $v_2$.

The set of boundary nodes $\mathcal{B}$ are the potential start and end nodes in the graph optimization. To define this set of boundary nodes, it may be necessary to first define boundary vertices in the delivery coordinate space for one-dimensional (1D) and two-dimensional (2D) spaces (which may be generalized to higher dimensions). A 1D space may be made of only vertices and edges, and boundary vertices are those which touch at most a single edge. Similarly, in a 2D space of vertices, edges and faces, boundary vertices are those which belong to an edge that only touches a single face. With this definition, a region $\mathcal{R}=(n_y,n_{subindex})$ may be a boundary region if one of the following conditions is satisfied:

(1) Vertex v of index n, is a boundary vertex;
(2) There exists an edge in the delivery coordinate space touching vertex v of index n, such that there is no region edge along this delivery coordinate space edge emanating from region r.

Figure 12A:
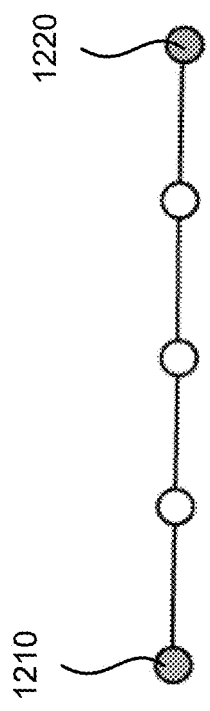
FIG. 12A illustrates boundary nodes in a one-dimensional (1D) delivery coordinate space according to some embodiments.
Figure 12B:
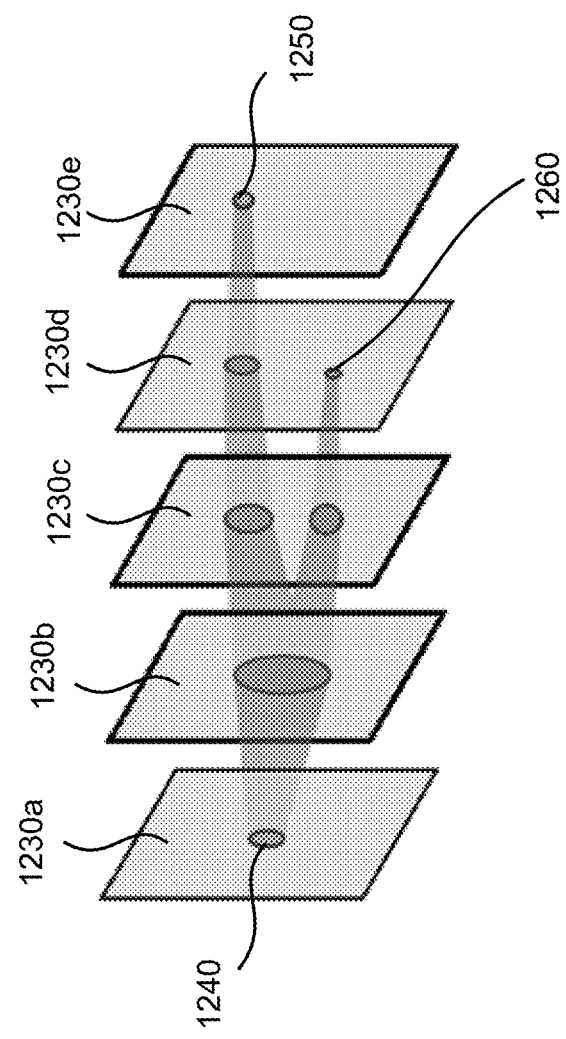
FIG. 12B illustrates boundary nodes in a two-dimensional (2D) delivery coordinate space according to some embodiments.

FIGS. 12A-12B illustrates these conditions. FIG. 12A may represent a 1D delivery coordinate space, with boundary vertices 1210 and 1220 represented as filled circles. FIG. 12B may represent a 2D delivery coordinate space. The BEV region connectivity manifold is represented by ovals (with each oval representing a region) in five BEV planes 1230a-1230e, and the connections between them. The region 1240 in the leftmost plane 1230a and the region 1250 on the rightmost plane 1230e are boundary regions that satisfy condition (1) above, while the region 1260 in the plane 1230d has no connection to a region on the right, thus is a boundary region that satisfy condition (2) above. With these definitions, a node is a boundary node if all the regions denoted by its region bitfield are boundary regions.

The state information used in the graph optimization is PTV angular flux $\mathcal{A}$. Using a bitset definition of PTV angular flux as described above, the successor function $\sigma$, which defines how the state changes, may be defined by the bitwise OR operator, $\sigma(\mathcal{A}_1,(N_1,N_2))=\mathcal{A}_1 | \mathcal{A}(N_2)$, where $q(N_2)$ is the contribution to the angular flux state from the regions denoted by region bitfield $b_2$ at vertex $v_2$.

Given two points $P_i=(N_i,\mathcal{A}_i)$ where $N_i=(v_i,c_i,b_i)$ for $i=1, 2$ with edge E connecting the nodes, min/max-distance functions may be defined as, $$D^{min}(P_1, P_2) = \Delta\theta(E)\left(\frac{3}{S(P_1, P_2)} + t^{mlc}(E) + p^{eff}(E)\right), \quad (8)$$

$$D^{max}(P_1, P_2) = \Delta\theta(E)S(P_1, P_2), \quad (9)$$

where $\Delta\theta$ is the physical angular distance traveled by the treatment head. The min-distance function is set to $+\infty$ if the resulting MLC configuration violates machine limitations. Note that the score term $S(P_1,P_2)$ appears as the inverse of one another in each equation, reflecting the fact that, roughly speaking, max-distance="goodness" and min-distance=1/"goodness". The definitions and meanings behind each term are as follows:

$$S(P_1,P_2) = S^{score}(b_2) + 2\, S^{angular}(\mathcal{A}_1,\mathcal{A}_2)$$

$$S^{score}(b) = \frac{\mathcal{R}_{avg}(b)+1}{2}\cdot \max(0, A(b) - A_{penalty}(b)),$$

where $\mathcal{R}_{avg}(b)$ is the average region score of the regions of bitfield b per unit area, $A(b)$ is the combined area of regions of bitfield b, and $A_{penalty}(b)$ is the total non-region area exposed by the fitted MLCs. This term penalizes poor MLC target fitting and encourages high scoring regions.

$S^{angular}(\mathcal{A}_1,\mathcal{A}_2)$ is a term that encourages regions that provide novel angles to the existing angular flux state. If $\mathcal{A}_{avg}$ is the average contribution (number of bits) to a blank angular flux state from each region, then $S^{angular}(\mathcal{A}_1,\mathcal{A}_2)$ is the number of bits in $(\mathcal{A}_2 \&\sim\mathcal{A}_1)$ or 1 (whichever is larger), normalized by dividing by $\mathcal{A}_{avg}$.

$t^{mlc}$ is the time for the MLCs to move between control points. This penalizes collimator angles that result in excessive MLC motion.

$p^{eff}=(1-\Delta\theta/\Delta\theta_{max})$ is a factor that penalizes edges where the trajectory is almost stationary, so treatment time is not wasted in such locations.

The score term $S(P_1, P_2)$ may be the main force driving the optimizer to find trajectories that target the PTV from good directions and that give contributions from different directions while avoiding poor MLC target fitting.

E. Graph Optimization Solution

The stateful dual-distance metric graph optimization defined above may be solved using the Dijkstra algorithm. Converting the list of points from the resulting optimal trajectory to control points may provide the desired radiotherapy trajectory. Running Dijkstra's algorithm from a start node without stopping at any particular end node may result in a tree structure of points, effectively completing a 1-to-N search from the given starting node to all other nodes with the same computational complexity as the usual 1-to-1 search between two nodes. By selecting the trajectory with the largest max-distance, the restricted optimization problem of finding the optimal trajectory from a given node may be solved efficiently.

In general, to find the globally optimal trajectory with the largest max-distance may require repeating this computation from every possible node (N-to-N search). An approximately optimal trajectory can be found by picking an arbitrary start node, and running this algorithm repeatedly with the same initial state, using the end node of the previous run as the start node of the successive run. In some embodiments, this process is repeated twice; thus trajectory optimization may be carried out with the same computational complexity as the underlying Dijkstra algorithm.

The path optimization may be carried out for each connected component of the graph. The trajectory with the largest max-distance across all possibilities may be selected in the end. The presence of the angular flux state in the distance function may help ensure that the selected trajectory will also be one that tends to provide novel directions from which to treat the PTV.

Figure 13:
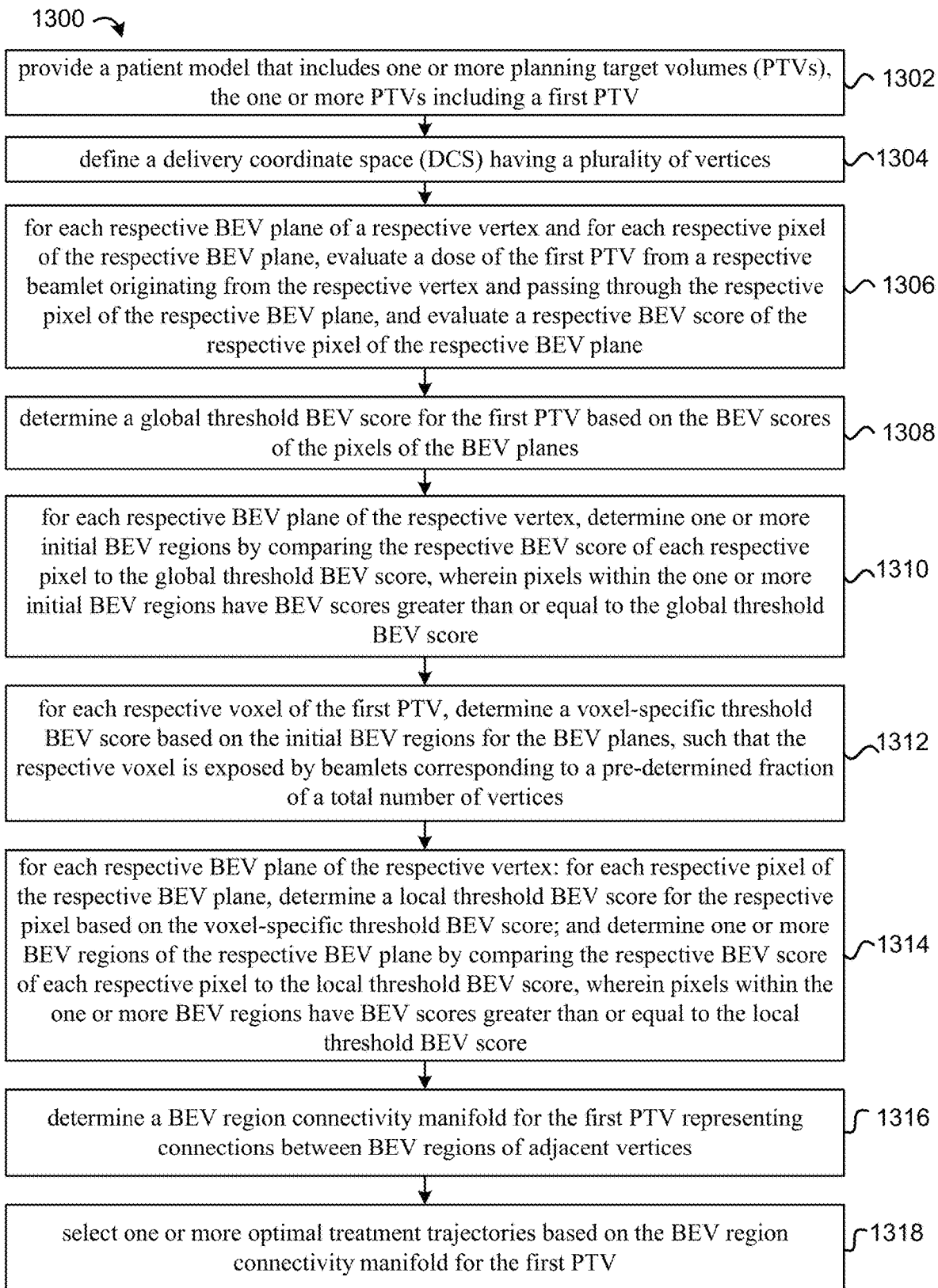
FIG. 13 shows a flowchart illustrating a method of trajectory optimization for radiotherapy treatment using sectioning with coverage boosting according to some embodiments.

F. Method of Trajectory Optimization for Radiotherapy Treatment Using Sectioning with Coverage Boosting FIG. 13 shows a flowchart illustrating a method 1300 of trajectory optimization for radiotherapy treatment using sectioning with coverage boosting according to some embodiments.

At 1302, a patient model is provided. The patient model includes one or more planning target volumes (PTVs), which includes a first PTV.

At 1304, a delivery coordinate space (DCS) is defined. The DCS may include a plurality of vertices. Each respective vertex defines a respective beam's eye view (BEV) plane.

At 1306, for each respective BEV plane of a respective vertex and for each respective pixel of the respective BEV plane, a dose of the first PTV from a respective beamlet originating from the respective vertex and passing through the respective pixel of the respective BEV plane is evaluated. A respective BEV score of the respective pixel of the respective BEV plane is also evaluated based at least in part on the dose of the first PTV from the respective beamlet.

At 1308, a global threshold BEV score for the first PTV is determined based on the BEV scores of the pixels of the BEV planes.

At 1310, for each respective BEV plane of the respective vertex, one or more initial BEV regions are determined by comparing the respective BEV score of each respective pixel to the global threshold BEV score. The pixels within the one or more initial BEV regions have BEV scores greater than or equal to the global threshold BEV score. Each respective initial BEV region may expose one or more voxels of the first PTV to beamlets corresponding to the respective vertex At 1312, for each respective voxel of the first PTV, a voxel-specific threshold BEV score is determined based on the initial BEV regions for the BEV planes, such that the respective voxel is exposed by beamlets corresponding to a pre-determined fraction of a total number of vertices.

At 1314, for each respective BEV plane of the respective vertex, and for each respective pixel of the respective BEV plane, a local threshold BEV score for the respective pixel is determined based on the voxel-specific threshold BEV score. One or more BEV regions of the respective BEV plane are determined by comparing the respective BEV score of each respective pixel to the local threshold BEV score. The pixels within the one or more BEV regions have BEV scores greater than or equal to the local threshold BEV score.

At 1316, a BEV region connectivity manifold is determined for the first PTV. The BEV region connectivity manifold represents connections between BEV regions of adjacent vertices.

At 1318, one or more optimal treatment trajectories are selected based on the BEV region connectivity manifold for the first PTV.

It should be appreciated that the specific steps illustrated in FIG. 13 provide a particular method of trajectory optimization for radiotherapy treatment according to some embodiments.

Other sequences of steps may also be performed according to alternative embodiments. For example, alternative embodiments may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

V. Trajectory Optimization for Multi-Target Radiotherapy Treatment

A radiotherapy treatment may treat multiple tumors or lesions that can have very different volumes. Some of the tumors may be partially or fully spatially overlapping, and some of them may be spatially disjoint. An example of a full spatial overlap may be a boost target inside a base planning target volume (PTV). Partial overlap may occur, for example, in head and neck treatments. Spatially disjoint lesions may be encountered as multiple intracranial metastases. For instance, a breast cancer treatment may involve multiple targets defined for breast tissue and associated nodal groups.

The original TORUS approach treats all PTV volumes as a single entity, in which the target-specific characteristics are not accounted for. For example, no record of a boost region within a PTV is kept. Also, volumetrically small targets may not be considered on an equal footing with volumetrically large targets. According to some embodiments, the TORUS approach may be generalized for radiotherapy treatment of multiple targets. In the following, various aspects of multi-target trajectory optimization are discussed.

A. PTV-Group-Specific Region Section

According to some embodiments, in a multi-target radiotherapy treatment, regions may be calculated for each target independently, while setting the weights of other PTVs to zero. By calculating score thresholds for each target separately, a more balanced approach to a complex multi-target treatment may be achieved. During optimization, the regions associated with each target for each BEV may make up an entire set of regions. To ensure each target is treated fairly in the optimization, both the integrated region scores associated with each target, and the number of points sampled in the target for the purpose of calculating PTV angular flux novelty, may be proportional to the overall weighting factors associated with the targets.

In some embodiments, the identity of each PTV group may be kept intact with regard to those of other PTV groups. Without loss of generality, it may be assumed that the NPV target structures are grouped into N groups with $1 \leq N \leq N_{PTV}$. In some embodiments, a target group may correspond to a volumetric region to which optimization objectives will be associated. In some other embodiments, a target group may comprise multiple partially or fully spatially overlapping volumes.

BEV regions ($\mathcal{R}_i$) may contain BEV maps at each vertex of the discretized delivery coordinate space (DCS) for each PTV group indexed as i=1, . . . , N. A vertex is a tuple $v=(r_{iso}, \{s_a\}_{a=1}^{N_a})$, where $r_{iso}$ is the isocenter position, and $s_a$ are generalized coordinates corresponding to mechanical axes of a treatment device. For instance, in the case of a C-arm linear accelerator and a constant isocenter, the vertices may assume the form $v_{C\text{-}arm}=(r_{iso}, \theta_{gantry}, \theta_{couch})$. As discussed above, the BEV regions $\mathcal{R}_i$ may indicate through which areas of the BEV maps PTV group i are to be irradiated. There may be one BEV map per PTV group at each vertex.

Figure 14:
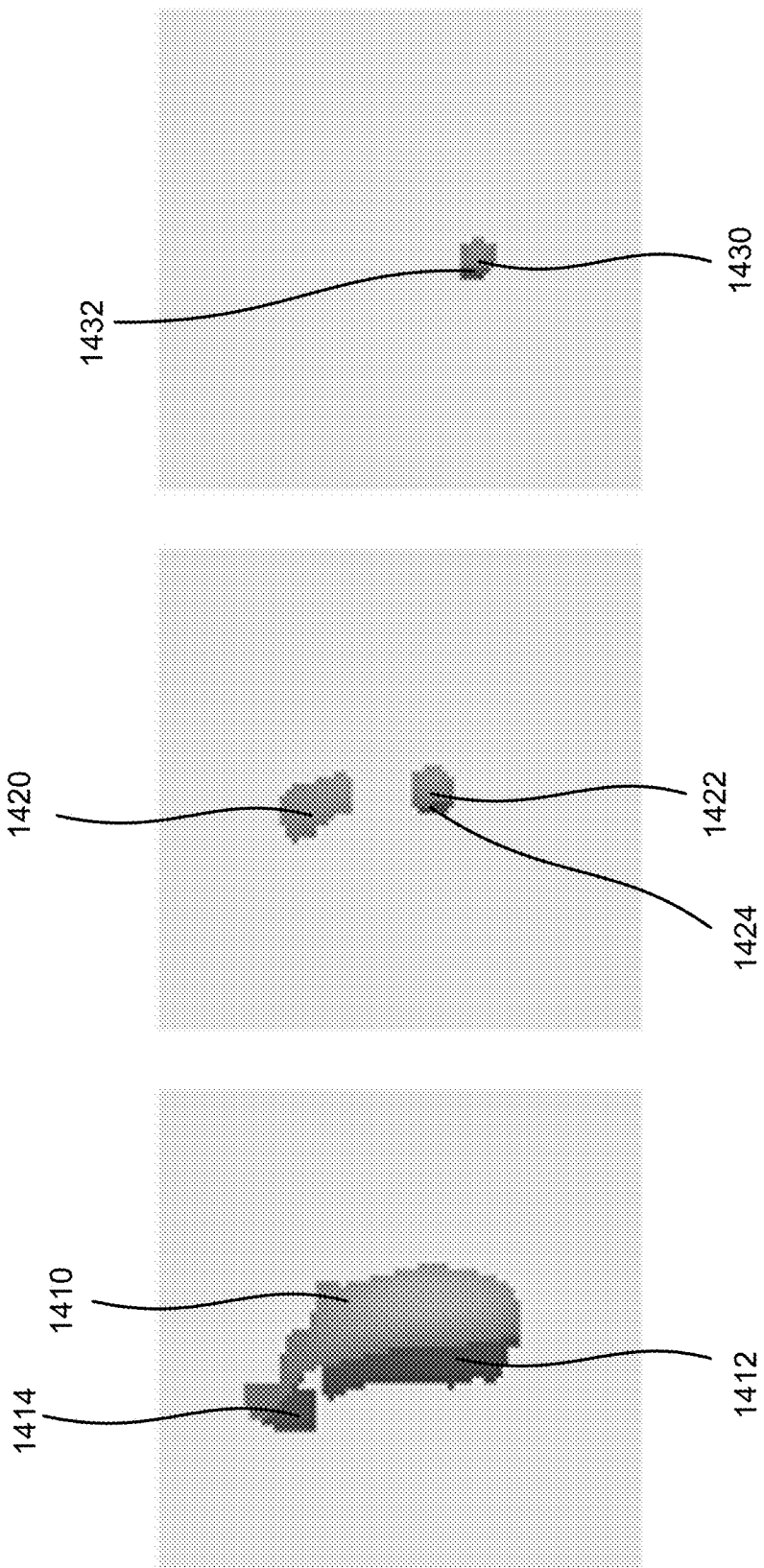
FIGS. 14A-14C show exemplary BEV maps of regions at the same vertex for three planning target volume (PTV) groups, respectfully, according to some embodiments.

FIGS. 14A-14C show exemplary BEV maps of the BEV regions $\mathcal{R}_i$ at the same vertex for three PTV groups (i=1, 2, 3). The areas 1410, 1420, 1422, and 1430 in gold color indicate BEV regions through which radiation may be administered to the targets. Information about the BEV regions 1410, 1420, 1422, and 1430 of each BEV may be stored in the associated region $\mathcal{R}_i$ (i=1, 2, 3). The dark areas 1414, 1424, and 1432 may correspond to regions irradiating through which may deposit either too little dose to the target group, or at too large an expense of healthy tissue or organs at risk (OAR). In some embodiments, the BEV regions 1410, 1420, 1422, and 1430 may have region scores in the range (0,1], and the dark areas 1414, 1424, and 1432 may have region scores in the range (−∞, 0] (e.g., as expressed in Equation (3) above).

In the examples illustrated in FIGS. 14A-14C, the BEV region 1410 in the BEV map shown in FIG. 14A may correspond to a main PTV (i=1), and the BEV regions 1420, 1430, and 1440 in the BEV maps shown in FIGS. 14B and 14C (i=2, 3) may correspond to sub PTVs inside the main PTV, to which boost doses of two different magnitudes may be delivered. These PTV groups are an example of full spatial overlap between PTVs; that is, the boost volumes shown in FIGS. 14B and 14C are volumetrically inside the main PTV shown in FIG. 14A.

The BEV regions $\mathcal{R}_i$ for all vertices for all PTV groups may make up an entire set of regions. In generating trajectories, a generalized TORUS algorithm may make decisions as which BEV regions 1410, 1420, 1422, and 1430 of which target groups are to be included in the MLC aperture at each direction of incidence.

B. PTV-Group-Specific Angular Point Density

As described above, one of the concepts in the TORUS methods is PTV angular flux, which characterizes how a set of elemental volumes (i.e. voxels) of a PTV is irradiated via a given beamlet. In the presence of multiple PTV groups, a generalized TORUS method may strive to irradiate each elemental volume of each PTV in each PTV group from as many directions as possible.

In some embodiments, a weighted volume $V_i$ for each PTV group may be calculated as:

$$v_j(x) = n_j(x) \Delta V(x); \quad (10)$$

$$g(x, \mathcal{J}_i) = \arg \max_{j \in \mathcal{J}_i} v_j(x); \quad (11)$$

$$\tilde{V}_i = \Sigma_{x \in V_i} \omega_{g(x,\mathcal{J}_i)}(x) v_{g(x,\mathcal{J}_i)}(x), \quad (12)$$

where $n_j(x)$ is the relative volume of voxel x occupied by PTV j, $\Delta V(x)$ is the volume of voxel x, the set $\mathcal{J}_i$ contains indices of PTVs in group i, and wj (x) are non-negative PTV-specific weights. Then, each PTV group i may be assigned an angular point density $n_{A,i}$ that reads, $$N_A(V) = \alpha V^\beta + \lambda; \quad (13)$$

$$n_{A,i} = N_A(V) \frac{\max_i \tilde{V}_i}{\tilde{V}_i V_{(\text{argmax}_j \tilde{V}_j)}}, \quad (14)$$

where $N_A(V)$ is a function that returns the number of sampled points, and α, β, and λ are parameters that may be tuned to maintain a sufficiently large point density at all relevant volumes V. In some embodiments, β may be a positive number that is less than unity.

In some embodiments, the PTV-specific weights, $\omega_j(x)$, may be the positive score coefficients, e.g., $w_{n_{ROI}}$ in Equation (2) above, which were used to compute the BEV-pixel-specific score region values. In some other embodiments, a different relative weighting among the PTV groups may be employed.

C. PTV-group-specific region connectivity manifolds

According to some embodiments, based on $\{\mathcal{R}_i\}_{i=1}^N$, a set $\{\mathcal{M}_i\}_{i=1}^N$ of region connectivity manifolds may be constructed. $\mathcal{M}_i$ keeps track of how and which PTV group i's regions in different connected vertices connect to one another. Edges (i.e., connections) may exist between neighboring vertices if the delivery device's configuration so allows. $\mathcal{M}_i$ maintains an ordered list of all regions $R_i^{(j)}$, j=1, . . . , $N_{R,i}$ through which PTV group i is to be irradiated, as well as a vertex-specific lists $R_i^{(v)}$, v∈$\mathcal{V}$ of regions in the set of vertices V of the DCS.

D. Collapsing of PTV-Specific BEV Maps into a Single Multi-PTV BEV Map

As discussed above and in Reference [1], TORUS uses a graph optimization method that is a modification of Dijkstra's algorithm, which outputs the entire tree of minimum distances from one starting node to all other nodes on the graph. According to some embodiments, to reduce the computational effort in the case of multiple PTV groups, one can resort to a strategy of contracting or collapsing PTV group-specific BEV maps onto a single multi-PTV BEV map. In one embodiment, the collapsing may be carried out on a BEV pixel-specific basis by assigning the multi-PTV BEV map the pixel value, $$p_{\text{multi-PTV}}^v(x, y) = \max_i p_i^v(x, y), \quad (15)$$

at pixel coordinate (x,y) for vertex v. In other embodiments, the collapsing may be carried out with other procedures that retain the property that if $r_i^v(x,y) \in (0,1]$ for some i, it remains within (0,1] on the collapsed map.

Figure 15:
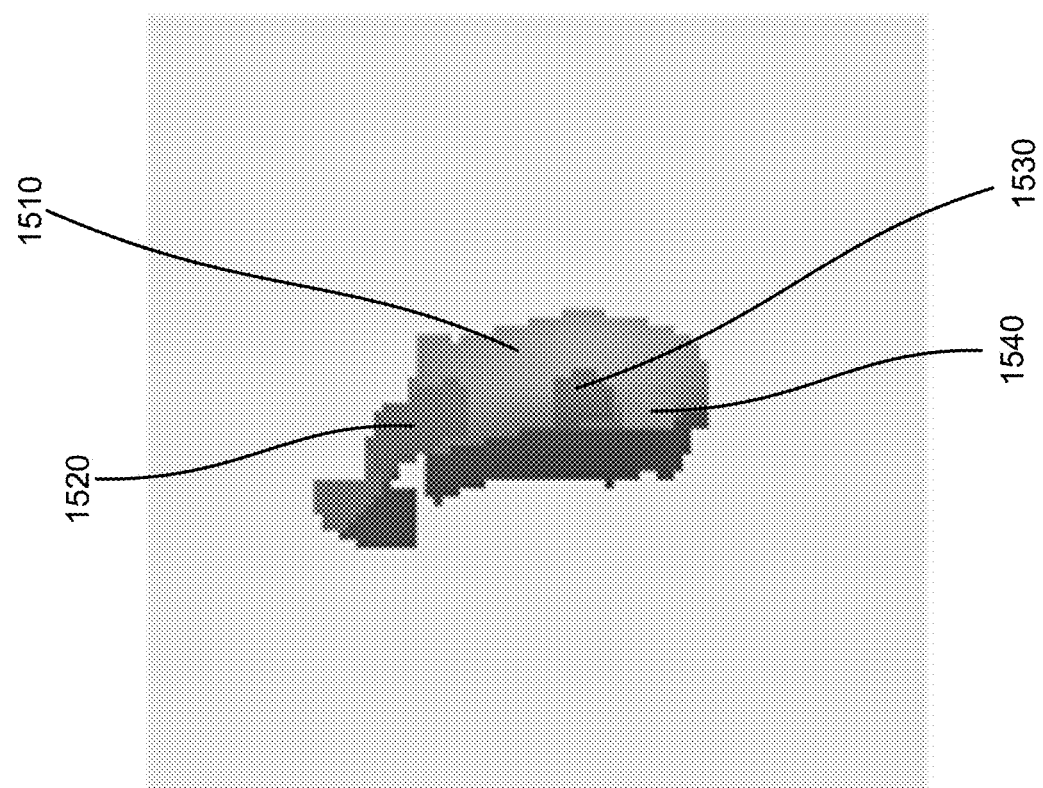
FIG. 15 shows an overlay of four regions that correspond to three different PTV groups according to some embodiments.

FIG. 15 shows an overlay of four regions 1510, 1520, 1530, and 1540 that correspond to three different PTV groups. The regions 1520 and 1530 shown in purple color and the region 1540 shown in green color correspond to subregions within which a collapse function has been used to assign a region value to the affected pixels in the BEV. As a result of collapsing, the identities of PTVs are lost and the subregions alone can no longer be included in an MLC aperture.

The collapsing strategy may reduce the number of regions if the size of overlap between the regions of different PTV groups exceeds a threshold, the minimum for which is one pixel. For spatially disjoint targets, the regions rarely overlap whereby they do not provide any computational improvement. On the other hand, computational improvement may occur in the case of multiple boost volumes that reside inside a base PTV.

Figure 16:
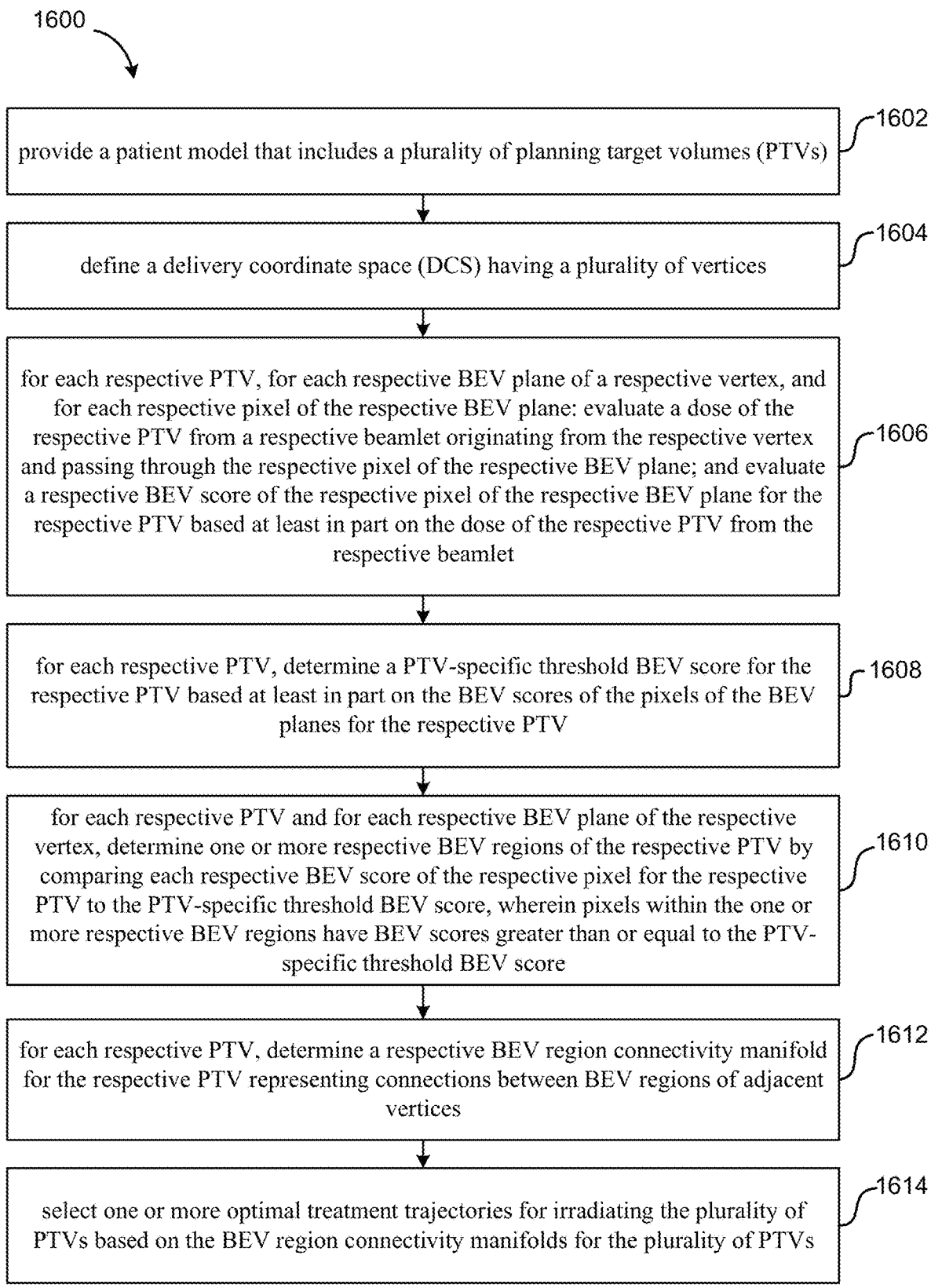
FIG. 16 shows a flowchart illustrating a method of trajectory optimization for radiotherapy treatment of multiple targets according to some embodiments.

E. Method of Trajectory Optimization for Radiotherapy Treatment of Multiple Targets FIG. 16 shows a flowchart illustrating a method of trajectory optimizaiton 1600 for radiotherapy treatment of multiple targets according to some embodiments.

At 1602, a patient model is provided. The patient model includes a plurality of planning target volumes (PTVs).

At 1604, a delivery coordinate space (DCS) is defined. The DCS includes a plurality of vertices. Each respective vertex defines a respective beam's eye view (BEV) plane.

At 1606, for each respective PTV of the plurality of PTVs, for each respective BEV plane of a respective vertex, and for each respective pixel of the respective BEV plane, a dose of the respective PTV from a respective beamlet originating from the respective vertex and passing through the respective pixel of the respective BEV plane is evaluated. A respective BEV score of the respective pixel of the respective BEV plane is also evaluated for the respective PTV based at least in part on the dose of the respective PTV from the respective beamlet.

At 1608, for each respective PTV of the plurality of PTVs, a PTV-specific threshold BEV score is determined for the respective PTV based at least in part on the BEV scores of the pixels of the BEV planes for the respective PTV.

At 1610, for each respective PTV of the plurality of PTVs and for each respective BEV plane of the respective vertex, one or more respective BEV regions of the respective PTV are determined by comparing each respective BEV score of the respective pixel for the respective PTV to the PTV-specific threshold BEV score. The pixels within the one or more respective BEV regions have BEV scores greater than or equal to the PTV-specific threshold BEV score.

At 1612, for each respective PTV of the plurality of PTVs, a respective BEV region connectivity manifold is determined for the respective PTV. The BEV region connectivity manifold represents connections between BEV regions of adjacent vertices.

At 1614, one or more optimal treatment trajectories are selected for irradiating the plurality of PTVs based on the BEV region connectivity manifolds for the plurality of PTVs.

It should be appreciated that the specific steps illustrated in FIG. 16 provide a particular method of trajectory optimization for radiotherapy treatment according to some embodiments.

Other sequences of steps may also be performed according to alternative embodiments. For example, alternative embodiments may perform the steps in a different order. Moreover, the individual steps may include multiple substeps that may be performed in various sequences as appropriate to the individual step. Furthermore, additional steps may be added and some steps may be removed depending on the particular applications. One of ordinary skill in the art would recognize many variations, modifications, and alternatives.

VI. Beam Angle Optimization Using Sectioning

The TORUS methods use the BEV regions and the BEV region connectivity manifold as a guide to generate heuristically optimal radiotherapy trajectories automatically for efficient delivery of high quality VMAT treatment plans. According to some embodiments, the TORUS methods are modified to generate heuristically optimal IMRT fields. As discussed above, the TORUS methods use an optimization graph on top of a delivery coordinate space to generate optimal treatment trajectories through the use of a dual-metric optimization. Nodes in the optimization graph represent individual control points, and trajectories are defined to be paths that minimize a min-distance metric, while a max-distance metric acts as a measure of goodness to select optimal trajectories. For an IMRT treatment plan, treatment fields may be represented in this framework as a set of nodes. A beam angle optimization may involve finding a set of k nodes that have optimal max-distance.

A. Field Geometry Optimization

According to some embodiments, to find a set of k beams, a BAO graph based on the TORUS graph concept may be built based on the following nodes and edges:

Nodes

Nodes are a set $\mathcal{N}$ N of N tuples of the form (v,c,b), where v is a vertex, c is the collimator angle index, and b is a binary mask of included regions. Each tuplet may determine a single field. The vertex v may correspond to a location in a discretized delivery coordinate space (DCS). For example, in a C-arm linear accelerator, the vertex v may correspond to an isocenter, a gantry angle $\theta_{gantry}$, and a couch angle $\theta_{couch}$. The collimator angle index c may correspond to a collimator angle $\theta_c$ out of a set of discrete possible collimator angles. The region mask b may correspond a set of contiguous target regions the MLC leaves may expose.

Edges

Edges are connections between neighbor nodes that have vertex-vertex connectivity in the underlying delivery coordinate space, and MLC connectivity between the respective MLC leaf sequences. In the case of beam angle optimization, the MLC connectivity constraint may not be important, but it may nevertheless act to reduce the number of edges in the graph. Thus, it may be computationally useful to keep the MLC connectivity constraint.

In the TORUS methods, a min-distance and a max-distance may be defined along edges use in the TORUS graph. In the case of static fields, there is no gantry motion while the treatment beam is on. Therefore, only the vertices themselves need to be considered, and there is no need for a min-distance function. The score (max-distance) may be the metric to optimize. The score S may be defined on subsets of nodes as, $$S(\mathcal{B}) = \text{max-distance corresponding to the set of nodes(beams)} \, \mathcal{B} \subset \mathcal{N}. \tag{16}$$

The optimal set of k beams may be defined to be the subset $B \subset \mathcal{N}$ with $|\mathcal{B}|=k$ that gives an optimal score $S(\mathcal{B})$, where $|\mathcal{B}|$ represents the number of beams in the subset $\mathcal{B} \subset \mathcal{N}$.

The score $S(\mathcal{B})$ may be a complex non-local function of the entire subset $\mathcal{B}$. Therefore, it may be a non-trivial problem to solve exactly. However, there may exist an efficient way to find approximate solutions faster than trying all $_NC_k$ combinations. In some embodiments, a beam angle optimization may include the following steps:

(1) Evaluate the scores for individual beams ($|\mathcal{B}|=1$), and use the squares of these scores as sampling probabilities.

(2) Randomly sample k beams using the sampling probabilities.

(3) Apply local gradient descent to this set $\mathcal{B}$ to find a local minimum.

(4) Repeat steps (1)-(3) until there is no improvement in score found for a predetermined number of successive trials (e.g., 20 successive trials).

This procedure may be referred to as a gradient descent method. During each iteration of the gradient descent procedure, all possible "edges" may be considered looking for improvement, where an "edge" is motion of the subset $\mathcal{B}$ to a neighbor subset $\mathcal{B}'$. The subset of beams may be updated to move in the direction that most improves the score. This procedure may be repeated until no more local improvements in the score is found. A neighbor to subset $\mathcal{B}$ is defined to be another subset $\mathcal{B}'$ that differs in exactly one beam $B_i \rightarrow B'_i$, where these two beams either share an edge in the TORUS graph or have the same position in the delivery coordinate space (same vertex).

B. Score Function

The score function $S(\mathcal{B})$ may be similar to the max-distance function as in TORUS. The score $S(\mathcal{B})$ of a set of beams $\mathcal{B}$ may include two parts: individual beam scoring, and overall PTV angular flux novelty. The presence of the global PTV angular flux metric is what makes the score function non-local, whereby it is not simply a function of the scores of the individual beams. The score $S(\mathcal{B})$ may be written as the sum of two parts, $$S(\mathcal{B}) = S_{local}(\mathcal{B}) + 3S_{flux}(\mathcal{B}), \tag{17}$$

where the local part $S_{local}(\mathcal{B})$ may be defined as $$S_{local}(\mathcal{B}) = \sum_{B \in \mathcal{B}} S_{beam}(B), \quad (18)$$

$$S_{beam}(B) = w(B) \cdot \left(\frac{s(B)}{A_{avg}} + \frac{0.2}{\max(0.05, o(B))}\right), \quad (19)$$

$$w(B) = \max(0.1, \min(1.0, 1.1 - c^2(B))), \quad (20)$$

$$c(B) = MLC \text{ contention severity}, \quad (21)$$

$$s(B) = \text{integrated score of regions}, \quad (22)$$

$$o(B) = \frac{2}{1 + CrossSection^2(B)} + x_{rms}(B)/2. \quad (23)$$

$A_{avg}$ may be defined to be the average area of regions. Thus, the term $$\frac{S(B)}{A_{avg}}$$

may be considered as the average region score. In some embodiments, the MLC contention severity may relate to $A_{penalty}$ defined above as the total non-region area exposed by the fitted MLCs. The cross section may be defined to be the y extent of the open MLC leaves normalized to the average diameter of regions as circles. $x_{rms}(B)$ may be defined as the root-mean-square x extent of open leaves. The flux part $S_{flux}(\mathcal{B})$ may be defined as the PTV angular flux novelty of the angular flux state generated by the selected regions, normalized by dividing by the average angular flux novelty of the individual regions. The separation of the score into local and non-local parts may allow some code optimizations to be done by pre-computing the contributions of individual beams to the local part.

C. Beam Angle Optimization Including Consideration of Beam-Off Time

Consider an IMRT treatment as an external-beam radiotherapy treatment, where the dose is delivered from k static beam locations $r_i=(v_i,c_i)$, $i=1, \ldots, k$, where the indices $v_i$ and $c_i$ correspond to vertex and collimator angle index, respectively. In a C-arm linear accelerator treatment system, a vertex may include an isocenter, a gantry angle, and a couch angle. In other types of external-beam radiation treatment systems, a vertex may include other treatment axes variables. The fluence delivered from each $r_i$ may be determined by way of a fluence-optimization scheme that distributes the fluence optimally between the $r_i$ such that clinical optimization objectives are fulfilled.

A dosimetrically optimal IMRT treatment plan may be found within a given delivery coordinate space by running fluence optimization and leaf sequencing for each permissible combination of $\{r_i\}_{i=1}^k$, and by picking the dosimetrically optimal one. However, this process may be impractical due to the large number of possible combinations. Moreover, it may be desirable that the patient and the patient's internal organs remain stationary during the administration of radiation for the delivered dose to match the planned dose. The longer the treatment takes, the more likely that the patient or the patient's internal organs may move during the treatment, and hence a higher probability of not delivering the intended dose to the target volumes.

The overall treatment time may be prolonged by the beam-off transition times from beam $r_i$ to $r_{i+1}$. The total beam-off transition time from beam $r_i$ to $r_{i+1}$ may be expressed as $\Delta t_{i,i+1} = \max_j \Delta t_{i,i+1}^{change_j}$, where the changes may include, but are limited to the following:

a time of $\Delta t_{i,i+1}^{move}$ to move machine axes from positions at vertex $v_i$ to those at $v_{i+1}$;

a time of $\Delta t_{i,i+1}^{collimator}$ to rotate the collimator from $c_i$ to $c_{i+1}$;

a time of $\Delta t_{i,i+1}^{imaging}$ of acquiring an image or multiple images for guidance of treatment between beams i and i+1.

A minimization of the aggregate beam-off time $$\Delta t = \sum_{i=1}^{k-1} \Delta t_{i,i+1}$$

may be an important part of the beam-selection problem. In some embodiments, a BAO algorithm may include constraints on picking beams that can be delivered in a time-efficient radiation order. In some other embodiments, the radiation order of the beams may be determined as a post-processing step.

D. Method of Beam Angle Optimization Using Sectioning

Figure 17:
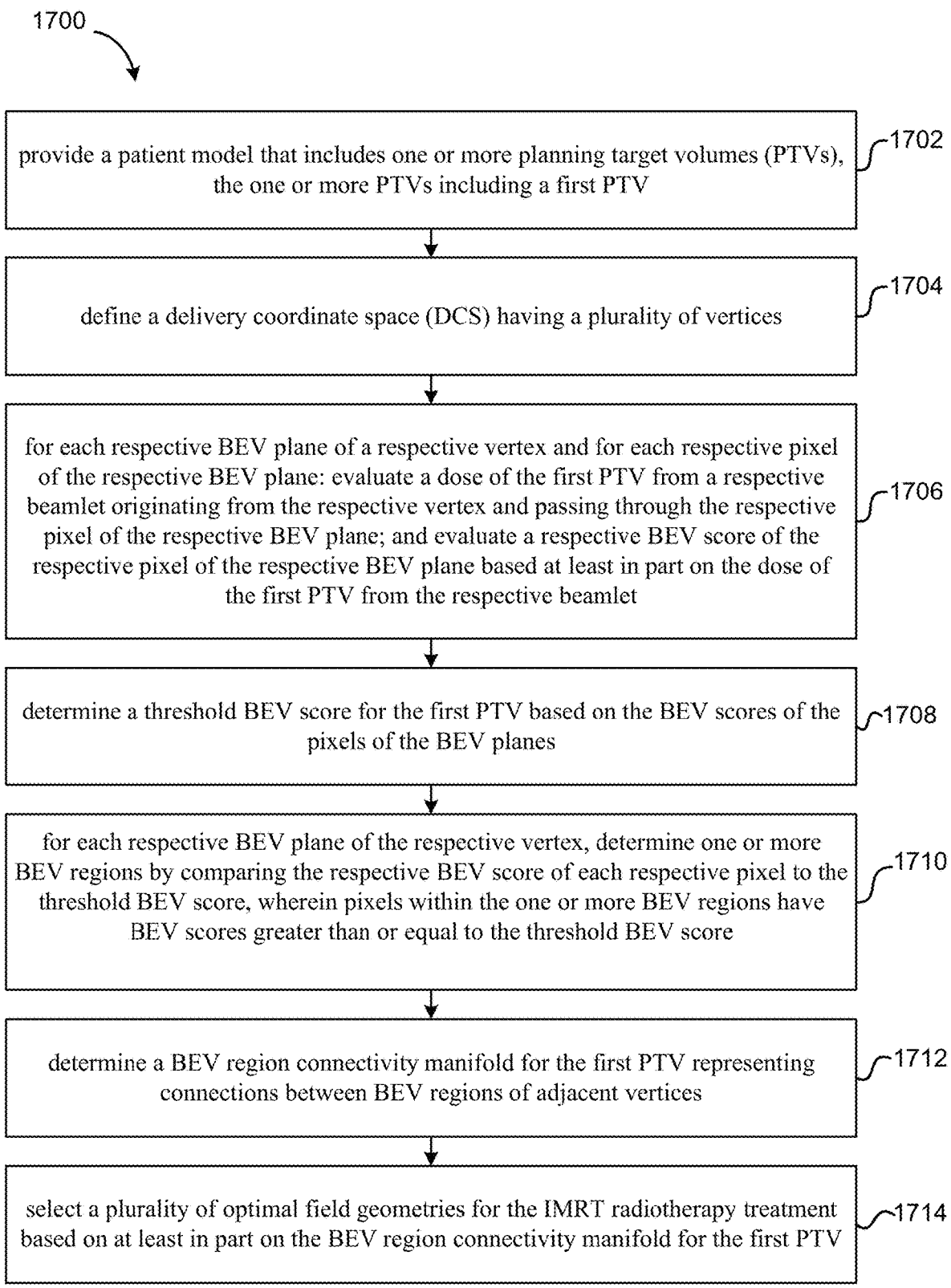
FIG. 17 shows a flowchart illustrating a method of beam angle optimization using sectioning according to some embodiments.

FIG. 17 shows a flowchart illustrating a method of beam angle optimizaiton 1700 using sectioning according to some embodiments.

At 1702, a patient model is provided. The patient model includes one or more planning target volumes (PTVs), which includes a first PTV.

At 1704, a delivery coordinate space (DCS) is defined. The DCS includes a plurality of vertices. Each respective vertex defines a respective beam's eye view (BEV) plane.

At 1706, for each respective BEV plane of a respective vertex and for each respective pixel of the respective BEV plane, a dose of the first PTV from a respective beamlet originating from the respective vertex and passing through the respective pixel of the respective BEV plane is evaluated. A respective BEV score of the respective pixel of the respective BEV plane is also evaluated based at least in part on the dose of the first PTV from the respective beamlet.

At 1708, a threshold BEV score is determined for the first PTV based on the BEV scores of the pixels of the BEV planes.

At 1710, for each respective BEV plane of the respective vertex, one or more BEV regions are determined by comparing the respective BEV score of each respective pixel to the threshold BEV score. The pixels within the one or more BEV regions have BEV scores greater than or equal to the threshold BEV score.

At 1712, a BEV region connectivity manifold is determined for the first PTV. The BEV region connectivity manifold represents connections between BEV regions of adjacent vertices.

At 1714, a plurality of optimal field geometries is selected for the IMRT radiotherapy treatment based on at least in part on the BEV region connectivity manifold for the first PTV.

It should be appreciated that the specific steps illustrated in FIG. 17 provide a particular method of beam angle optimization according to some embodiments. Other sequences of steps may also be performed according to alternative embodiments. For example, alternative embodiments may perform the steps in a different order. Moreover, the individual steps may include multiple sub-steps that may

Figure 18:
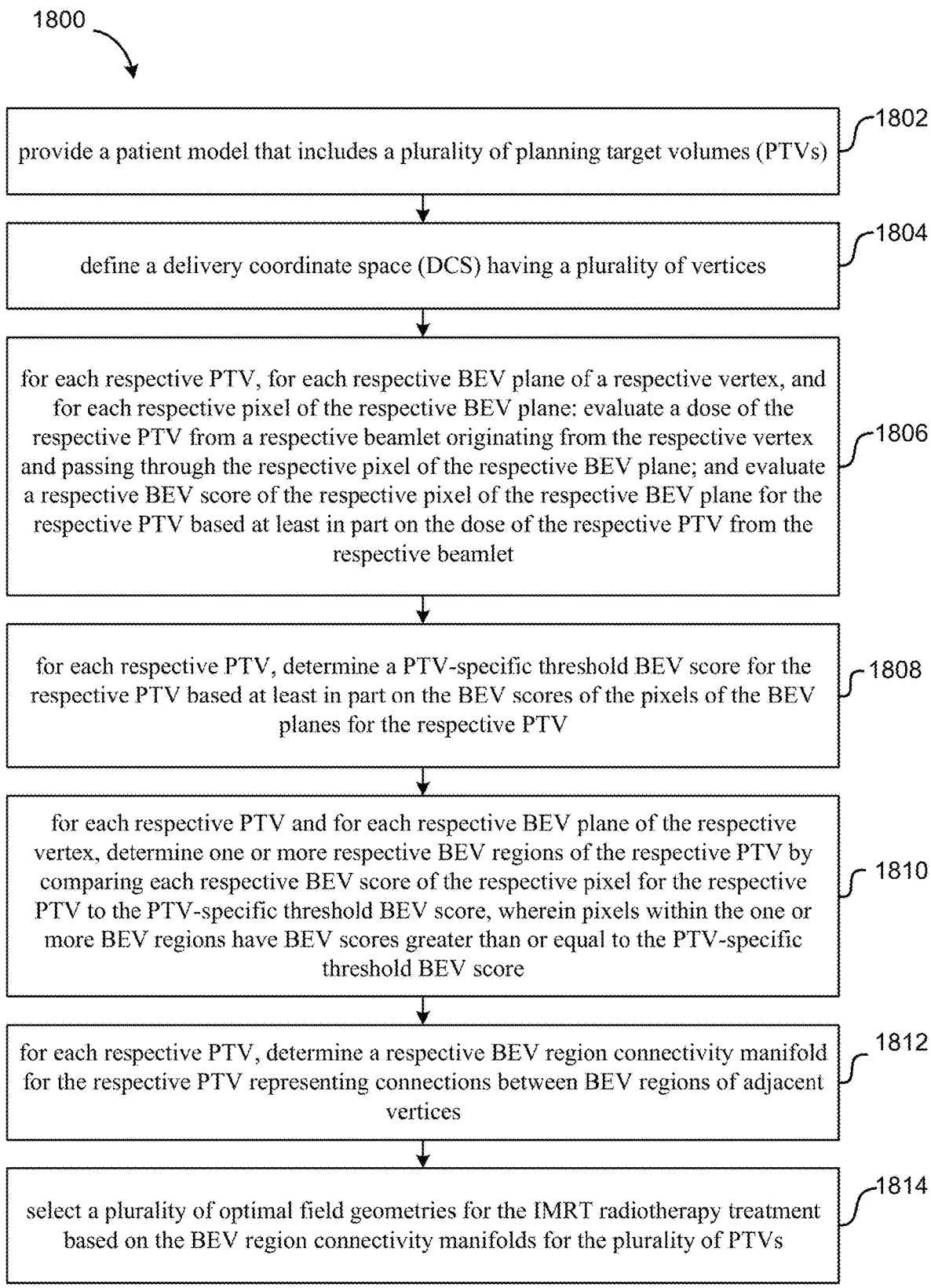
FIG. 18 shows a flowchart illustrating a method of beam angle optimization using sectioning according to some embodiments.

E. Method of Beam Angle Optimization for Radiotherapy Treatment of Multiple Targets FIG. 18 shows a flowchart illustrating a method of beam angle optimizaiton 1800 for radiotherapy treatment of multiple targets according to some embodiments.

At 1802, a patient model is provided. The patient model includes a plurality of planning target volumes (PTVs).

At 1804, a delivery coordinate space (DCS) is define. The DCS includes a plurality of vertices. Each respective vertex defines a respective beam's eye view (BEV) plane.

At 1806, for each respective PTV of the plurality of PTVs, for each respective BEV plane of a respective vertex, and for each respective pixel of the respective BEV plane: a dose of the respective PTV from a respective beamlet originating from the respective vertex and passing through the respective pixel of the respective BEV plane is evaluated. A respective BEV score of the respective pixel of the respective BEV plane is also evaluated for the respective PTV based at least in part on the dose of the respective PTV from the respective beamlet.

At 1808, for each respective PTV of the plurality of PTVs, a PTV-specific threshold BEV score is determined for the respective PTV based at least in part on the BEV scores of the pixels of the BEV planes for the respective PTV.

At 1810, for each respective PTV of the plurality of PTVs and for each respective BEV plane of the respective vertex, one or more respective BEV regions of the respective PTV are determined by comparing each respective BEV score of the respective pixel for the respective PTV to the PTV-specific threshold BEV score. The pixels within the one or more BEV regions have BEV scores greater than or equal to the PTV-specific threshold BEV score.

At 1812, for each respective PTV of the plurality of PTVs, a respective BEV region connectivity manifold is determined for the respective PTV. The BEV region connectivity manifold represents connections between BEV regions of adjacent vertices.

At 1814, a plurality of optimal field geometries is selected for the IMRT radiotherapy treatment based on the BEV region connectivity manifolds for the plurality of PTVs.

It should be appreciated that the specific steps illustrated in FIG. 18 provide a particular method of beam angle optimization according to some embodiments. Other sequences of steps may also be performed according to alternative embodiments. For example, alternative embodiments may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

Figure 19:
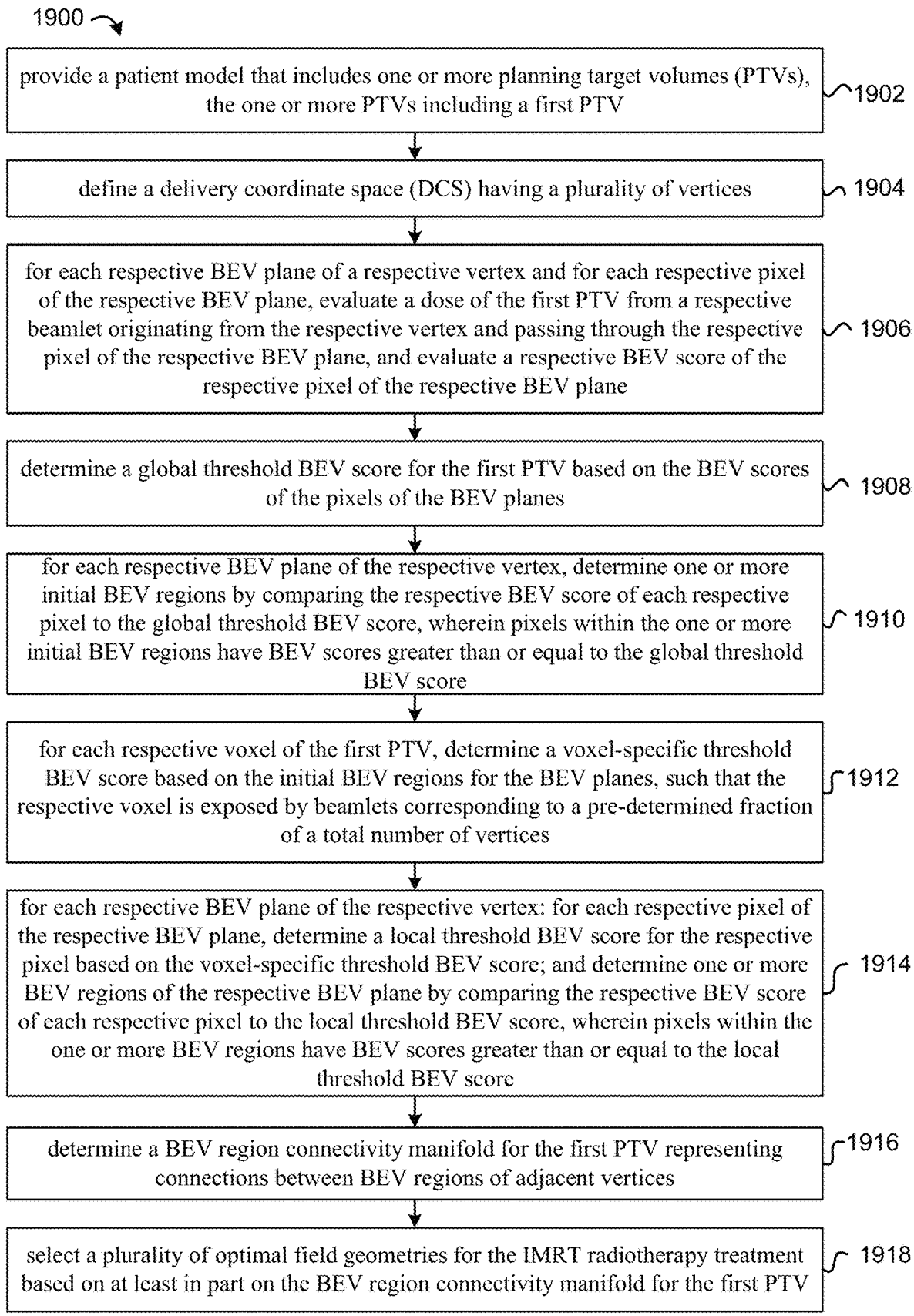
FIG. 19 shows a flowchart illustrating a method of beam angle optimization using sectioning with coverage boosting according to some embodiments.

F. Method of Beam Angle Optimization Using Sectioning with Coverage Boosting FIG. 19 shows a flowchart illustrating a method of beam angle optimizaiton 1800 using sectioning with coverage boosting according to some embodiments.

At 1902, a patient model is provided. The patient model includes one or more planning target volumes (PTVs), which includes a first PTV.

At 1904, a delivery coordinate space (DCS) is defined. The DCS may include a plurality of vertices. Each respective vertex defines a respective beam's eye view (BEV) plane.

At 1906, for each respective BEV plane of a respective vertex and for each respective pixel of the respective BEV plane, a dose of the first PTV from a respective beamlet originating from the respective vertex and passing through the respective pixel of the respective BEV plane is evaluated. A respective BEV score of the respective pixel of the respective BEV plane is also evaluated based at least in part on the dose of the first PTV from the respective beamlet.

At 1908, a global threshold BEV score for the first PTV is determined based on the BEV scores of the pixels of the BEV planes.

At 1910, for each respective BEV plane of the respective vertex, one or more initial BEV regions are determined by comparing the respective BEV score of each respective pixel to the global threshold BEV score. The pixels within the one or more initial BEV regions have BEV scores greater than or equal to the global threshold BEV score. Each respective initial BEV region may expose one or more voxels of the first PTV to beamlets corresponding to the respective vertex.

At 1912, for each respective voxel of the first PTV, a voxel-specific threshold BEV score is determined based on the initial BEV regions for the BEV planes, such that the respective voxel is exposed by beamlets corresponding to a pre-determined fraction of a total number of vertices.

At 1914, for each respective BEV plane of the respective vertex, and for each respective pixel of the respective BEV plane, a local threshold BEV score for the respective pixel is determined based on the voxel-specific threshold BEV score. One or more BEV regions of the respective BEV plane are determined by comparing the respective BEV score of each respective pixel to the local threshold BEV score. The pixels within the one or more BEV regions have BEV scores greater than or equal to the local threshold BEV score.

At 1916, a BEV region connectivity manifold is determined for the first PTV. The BEV region connectivity manifold represents connections between BEV regions of adjacent vertices.

At 1918, a plurality of optimal field geometries is selected for the IMRT radiotherapy treatment based on at least in part on the BEV region connectivity manifold for the first PTV.

It should be appreciated that the specific steps illustrated in FIG. 19 provide a particular method of beam angle optimization according to some embodiments. Other sequences of steps may also be performed according to alternative embodiments. For example, alternative embodiments may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

VII. Computer System

Figure 20:
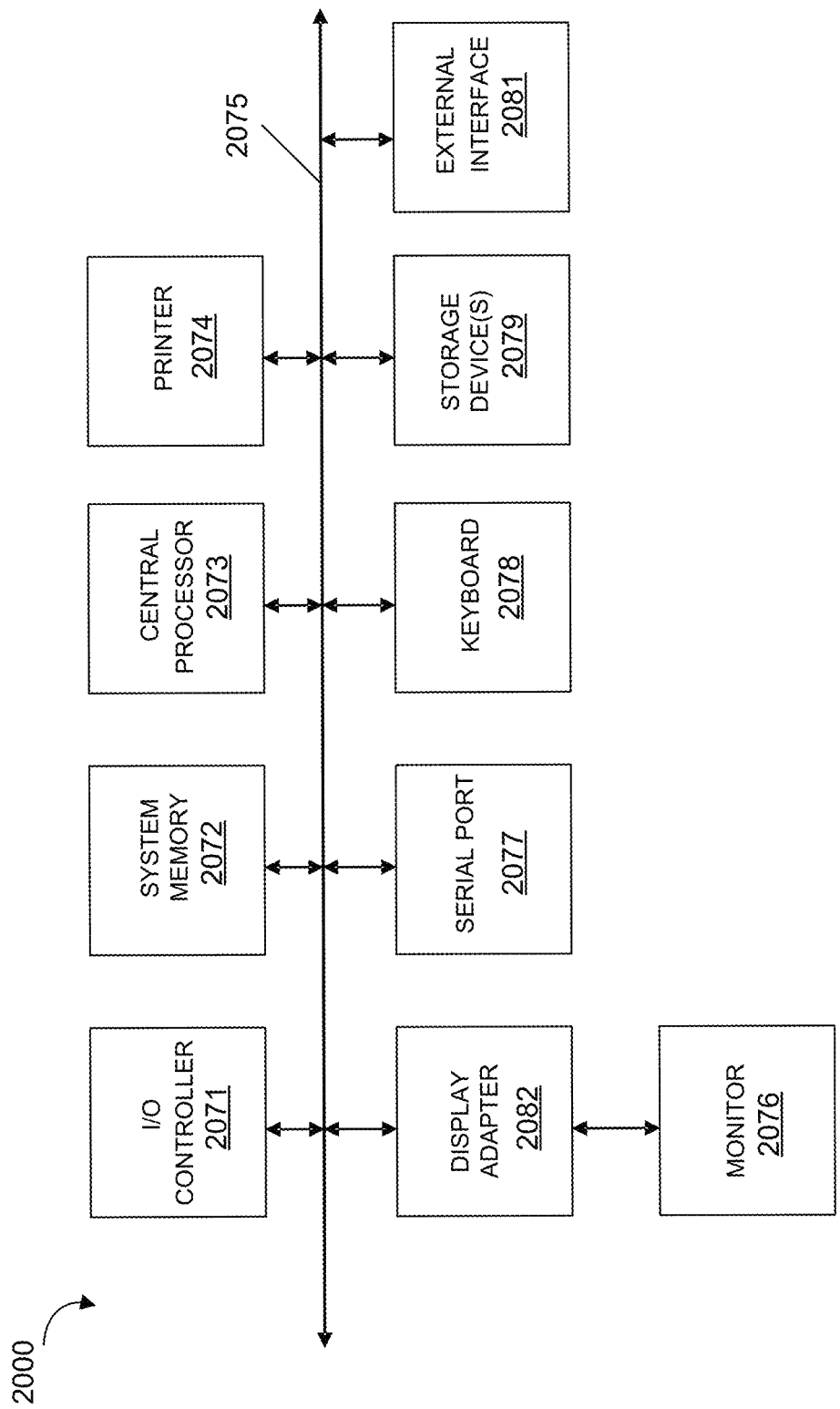
FIG. 20 shows a block diagram of an example computer system usable with system and methods according to embodiments.

Any of the computer systems mentioned herein may utilize any suitable number of subsystems. Examples of such subsystems are shown in FIG. 20 in computer system 2000. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 20 are interconnected via a system bus 2075. Additional subsystems such as a printer 2074, keyboard 2078, storage device(s) 2079, monitor 2076, which is coupled to display adapter 2082, and others are shown. Peripherals and input/output (I/O) devices, which couple to I/O controller 2071, can be connected to the computer system by any number of means known in the art, such as serial port 2077. For example, serial port 2077 or external interface 2081 (e.g. Ethernet, Wi-Fi, etc.) can be used to connect computer system 2000 to a wide area network such as the Internet, a mouse input device, or a scanner. The interconnection via system bus 2075 allows the central processor 2073 to communicate with each subsystem and to control the execution of instructions from system memory 2072 or the storage device(s) 2079 (e.g., a fixed disk, such as a hard drive or optical disk), as well as the exchange of information between subsystems. The system memory 2072 and/or the storage device(s) 2079 may embody a computer readable medium. Any of the data mentioned herein can be output from one component to another component and can be output to the user.

A computer system can include a plurality of the same components or subsystems, e.g., connected together by external interface 2081 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

External interface 2081 can be used to transmit one or more treatment plans to one or more radiation treatment devices, as described herein. For example, a treatment planning application can reside on a server computer, and a client computer can use the treatment planning application. The server computer can be part of a cloud computing platform that provides software as a service (SaaS). Once a treatment plan is determined, a client computer can specify which radiation device or a treatment plan database accessible by the radiation device for transmitting one or more files encapsulating the treatment plan. For instance, an IP address can be specified.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

REFERENCES

[1] Christopher Barry Locke and Karl Kenneth Bush. Trajectory optimization in radiotherapy using sectioning (TORUS). Medical Physics, 2017.

What is claimed is:
1. A method of trajectory optimization for radiotherapy treatment of multiple targets, the method comprising:
providing a patient model including a plurality of planning target volumes (PTVs);

defining a delivery coordinate space (DCS) having a plurality of vertices, each respective vertex defining a respective beam's eye view (BEV) plane;
for each respective PTV of the plurality of PTVs:
for each respective BEV plane of a respective vertex:
for each respective pixel of the respective BEV plane:
evaluating a dose of the respective PTV from a respective beamlet originating from the respective vertex and passing through the respective pixel of the respective BEV plane; and
evaluating a respective BEV score of the respective pixel of the respective BEV plane for the respective PTV based at least in part on the dose of the respective PTV from the respective beamlet;
determining a PTV-specific threshold BEV score for the respective PTV based at least in part on the BEV scores of the pixels of the BEV planes for the respective PTV;
for each respective BEV plane of the respective vertex:
determining one or more respective BEV regions of the respective PTV by comparing each respective BEV score of the respective pixel for the respective PTV to the PTV-specific threshold BEV score, wherein pixels within the one or more respective BEV regions have BEV scores greater than or equal to the PTV-specific threshold BEV score; and
determining a respective BEV region connectivity manifold for the respective PTV representing connections between BEV regions of adjacent vertices; and
selecting one or more optimal treatment trajectories for irradiating the plurality of PTVs based on the BEV region connectivity manifolds for the plurality of PTVs.

2. The method of claim 1, wherein the one or more optimal treatment trajectories comprise one or more VMAT arcs.

3. The method of claim 1, wherein each vertex in the DCS comprises an isocenter, a gantry angle, and a couch angle.

4. The method of claim 1, wherein selecting the one or more optimal treatment trajectories comprises performing a stateful graph optimization.

5. The method of claim 4, wherein the stateful graph optimization is performed on a graph defined by a plurality of nodes, each node associated with a respective vertex in the DCS and a state relating to a set of PTV angular fluxes for a set of sampling points distributed among the plurality of PTVs, each PTV angular flux relating to novelty of directional vectors of incident beamlets through a closed surface centered at a respective sampling point of the set of sampling points.

6. The method of claim 5, wherein the closed surface comprises a quadrilateralized spherical cube.

7. The method of claim 5, wherein the set of sampling points is distributed among the plurality of PTVs according to weighting factors associated with the plurality of PTVs.

8. The method of claim 5, wherein the set of sampling points is distributed among the plurality of PTVs such that a point density for each respective PTV is a decreasing function of a volume of the respective PTV.

9. The method of claim 4, wherein selecting the one or more optimal treatment trajectories comprises:

selecting a plurality of candidate trajectories that minimize a min-distance function based on the BEV region connectivity manifolds for the plurality of PTVs; and
selecting the one or more optimal treatment trajectories among the plurality of candidate trajectories that maximize a max-distance function.

10. The method of claim 9, further comprising:
for each respective PTV of the plurality of PTVs:
for each respective BEV plane of a respective vertex:
determining a region score for each respective pixel of the respective BEV plane based on the respective BEV score of the respective pixel; and
determining an average region score for each respective BEV region of the one or more BEV regions based on the region scores of the pixels of the respective BEV region;
wherein the min-distance function is inversely proportional to the average region score of each respective BEV region for each respective PTV, and the max-distance function is proportional to the average region score of each respective BEV region for the respective PTV.

11. The method of claim 10, wherein the region score for each respective pixel has a normalized positive value if the respective pixel is within one of the one or more BEV regions, and a negative value if the respective pixel is not within any of the one or more BEV regions.

12. The method of claim 10, wherein the average region score of each respective BEV region for each respective PTV is given a respective weight associated with the respective PTV.

13. The method of claim 10, further comprising:
for each respective BEV plane of a respective vertex for a subset of the plurality of vertices of the DCS:
collapsing a first BEV region of a first PTV of the plurality of PTVs and a second BEV region of a second PTV of the plurality of PTVs into a single BEV region.

14. The method of claim 1, wherein the patient model further includes an organ at risk (OAR), the method further comprising:
for each respective BEV plane of a respective vertex:
for each respective pixel of the respective BEV plane:
evaluating a dose of the OAR from a respective beamlet originating from the respective vertex and passing through the respective pixel of the respective BEV plane;
wherein evaluating the respective BEV score of the respective pixel of the respective BEV plane for the respective PTV comprises evaluating a weighted combination of the dose of the respective PTV and the dose of the OAR from the respective beamlet.

15. The method of claim 14, wherein the dose of the respective PTV is assigned a positive weight, and the dose of the OAR is assigned a negative weight.

16. The method of claim 1, wherein the plurality of PTVs includes a first PTV and a second PTV that fully or partially overlap with each other spatially.

17. The method of claim 1, wherein the plurality of PTVs includes a first PTV and a second PTV that are spatially disjoint with each other.

18. A method of trajectory optimization for radiotherapy treatment, the method comprising:
providing a patient model including one or more planning target volumes (PTVs), the one or more PTVs including a first PTV;

defining a delivery coordinate space (DCS) having a plurality of vertices, each respective vertex defining a respective beam's eye view (BEV) plane;
for each respective BEV plane of a respective vertex:
for each respective pixel of the respective BEV plane:
evaluating a dose of the first PTV from a respective beamlet originating from the respective vertex and passing through the respective pixel of the respective BEV plane; and
evaluating a respective BEV score of the respective pixel of the respective BEV plane based at least in part on the dose of the first PTV from the respective beamlet;
determining a global threshold BEV score for the first PTV based on the BEV scores of the pixels of the BEV planes;
for each respective BEV plane of the respective vertex:
determining one or more initial BEV regions by comparing the respective BEV score of each respective pixel to the global threshold BEV score, wherein pixels within the one or more initial BEV regions have BEV scores greater than or equal to the global threshold BEV score, and each respective initial BEV region exposes one or more voxels of the first PTV to beamlets corresponding to the respective vertex;
for each respective voxel of the first PTV:
determining a voxel-specific threshold BEV score based on the initial BEV regions for the BEV planes, such that the respective voxel is exposed by beamlets corresponding to a pre-determined fraction of a total number of vertices;
for each respective BEV plane of the respective vertex:
for each respective pixel of the respective BEV plane:
determining a local threshold BEV score for the respective pixel based on the voxel-specific threshold BEV score; and
determining one or more BEV regions of the respective BEV plane by comparing the respective BEV score of each respective pixel to the local threshold BEV score, wherein pixels within the one or more BEV regions have BEV scores greater than or equal to the local threshold BEV score;
determining a BEV region connectivity manifold for the first PTV representing connections between BEV regions of adjacent vertices; and
selecting one or more optimal treatment trajectories based on the BEV region connectivity manifold for the first PTV.

19. The method of claim 18, wherein selecting the one or more optimal treatment trajectories comprises performing a stateful graph optimization on a graph defined by a plurality of nodes, each node associated with a respective vertex in the DCS and a state relating to a set of PTV angular fluxes for a set of sampling points distributed within the first PTV, each PTV angular flux relating to novelty of directional vectors of incident beamlets through a closed surface centered at a respective sampling point of the set of sampling points.

20. The method of claim 19, wherein selecting the one or more optimal treatment trajectories comprises:
selecting a plurality of candidate trajectories that minimize a min-distance function based on the BEV region connectivity manifold for the first PTV; and
selecting the one or more optimal treatment trajectories among the plurality of candidate trajectories that maximize a max-distance function.

* * * * *